United States Patent
Zhuo

(10) Patent No.: US 8,185,323 B1
(45) Date of Patent: May 22, 2012

(54) METHOD OF IDENTIFYING EXONS AND INTRONS AND DIAGNOSTIC USES THEREOF

(76) Inventor: Degen Zhuo, Chapel Hill, NC (US)

( * ) Notice: Subject to any disclaimer, the term of this patent is extended or adjusted under 35 U.S.C. 154(b) by 1144 days.

(21) Appl. No.: 12/006,898

(22) Filed: Jan. 6, 2008

(51) Int. Cl.
*G06F 19/00* (2011.01)
*G06F 17/30* (2006.01)

(52) U.S. Cl. .......................... 702/20; 707/706
(58) Field of Classification Search .......... None
See application file for complete search history.

(56) References Cited

U.S. PATENT DOCUMENTS

| | | | |
|---|---|---|---|
| 5,612,179 A | 3/1997 | Simons | 435/6 |
| 6,977,165 B2 | 12/2005 | Farmer | 435/91.41 |

OTHER PUBLICATIONS

Zhuo, D., Madden, R., Elela, S. A. & Chabot, B. Modern origin of numerous alternatively spliced human introns from tandem arrays. Proc Natl Acad Sci U S A 104, 882-6 (2007).
Rodriguez-Trelles, F., Tarrio, R. & Ayala, F. J. Origins and evolution of spliceosomal introns. Annu Rev Genet 40, 47-76 (2006).
Roy, S. W. & Gilbert, W. The evolution of spliceosomal introns: patterns, puzzles and progress. Nat Rev Genet 7, 211-21 (2006).
Koonin, E. V. The origin of introns and their role in eukaryogenesis: a compromise solution to the introns-early versus introns-late debate? Biol Direct 1, 22 (2006).
Artamonova, II & Gelfand, M. S. Comparative genomics and evolution of alternative splicing: the pessimists' science. Chem Rev 107, 3407-30 (2007).
Xing, Y. & Lee, C. Alternative splicing and RNA selection pressure—evolutionary consequences for eukaryotic genomes. Nat Rev Genet 7, 499-509 (2006).
Nielsen, C. B., Friedman, B., Birren, B., Burge, C. B. & Galagan, J. E. Patterns of intron gain and loss in fungi. PLoS Biol 2, e422 (2004).
Jeffares, D. C., Mourier, T. & Penny, D. The biology of intron gain and loss. Trends Genet 22, 16-22 (2006).
Roy, S. W. The origin of recent introns: transposons? Genome Biol 5, 251 (2004).
Graveley, B. R. Mutually exclusive splicing of the insect Dscam pre-mRNA directed by competing intronic RNA secondary structures. Cell 123, 65-73 (2005).
Koonin, E. V. Temporal order of evolution of DNA replication systems inferred by comparison of cellular and viral DNA polymerases. Biol Direct 1, 39 (2006).
Sakurai, A. et al. On biased distribution of introns in various eukaryotes. Gene 300, 89-95 (2002).
Bonen, L. & Calixte, S. Comparative analysis of bacterial-origin genes for plant mitochondrial ribosomal proteins. Mol Biol Evol 23, 701-12 (2006).
Ruvinsky, A. & Ward, W. A gradient in the distribution of introns in eukaryotic genes. J Mol Evol 63, 136-41 (2006).
Lin, K. & Zhang, D. Y. The excess of 5' introns in eukaryotic genomes. Nucleic Acids Res 33, 6522-7 (2005).
Ast, G. How did alternative splicing evolve? Nat Rev Genet 5, 773-82 (2004).

*Primary Examiner* — John S Brusca

(57) ABSTRACT

Novel introns and exons are detected by selecting for a specific group of known correlating splice junctions, then searching for unknown introns and exons within that group. Also, diseases are detected by selecting for introns and exons associated with diseases or mutations. Detections are achieved using comparative genomics, gel electrophoresis or protein chip technologies.

15 Claims, 31 Drawing Sheets

METHOD OF IDENTIFYING EXONS AND INTRONS AND DIAGNOSTIC USES THEREOF

FIELD OF THE INVENTION

The invention herein pertains to methods of identifying introns and exons in genes by locating characteristic markers in splicing junctions employing standard amplification methods with comparative genomic, electrophoretic or protein chip technologies.

DESCRIPTION OF THE BACKGROUND AND OBJECTIVES OF THE INVENTION

Prokaryotic genes differ from eukaryotic genes in that every base pair in a prokaryotic gene is reflected in the mRNA base sequence. In eukaryotic genes there are often intervening sequences (introns) that do not appear in the mRNA base sequence for the gene product. The DNA sequences that are expressed and retained in the final mRNA product are "exons".

The entire DNA sequence, including exons and introns, are transcribed to produce a precursor hnRNA of the mature mRNA. However, during the splicing of pre-mRNA the introns are excised out and the exons are spliced together via two-step trans-esterification reactions carried out by the spliceosome, which consists of five ribonucleoprotein particles (RNPs). Genes from eukaryotic organisms contain a variable number of introns of varying sizes. For example, the gene for mouse Tbc1d2 gene encoding TBC1 domain family, member 2 contains 12 introns, the mouse Col1a1 gene coding for procollagen, type I, alpha 1, contains 50 introns.

The excision or splicing of spliceosomal introns occurs in the cell nucleus and is mediated by splicosome which consists of five ribonucleoprotein particles (RNPs). The splicosomal intron comprises a 5' splice site, 3' splice site and branch site. The spliceosomal small nuclear RNAs have highly conserved secondary structures similar to domains of self-splicing group II introns which are thought to be ancestors of the spliceosomal introns.

Ever since their discovery about 30 years ago, introns have intrigued the scientific community and stimulated debate about the nature and timing of their origin. There has also been curiosity about the apparent recent explosion in intron number in mammals and its contribution to expanded protein diversity and regulation through alternative splicing pathways. Correct removal of introns from genes has become a central issue in the medical research field. Otherwise, it leads to various human diseases such as cancers, autosomal recessive disorder, spinal muscular atrophy. However there are no methods to accurately identify the introns, that is, to accurately define exon/intron boundaries. We recently reported that many newly-acquired introns in the human genome share a signature of identical 5' and 3' splicing junctions consistent with an origin via segmental DNA duplication. It makes possible to accurately predict and annotation of mammalian genes and opens up many possibilities to identify novel control trans- or cis-elements and to predict novel alternatively spliced mRNA isoforms.

The specific markers are 20 bp upstream (E5) and 20 bp downstream (I5) nucleotides of 5' splicing sites and 20 bp upstream (I3) and 20 bp downstream (E3) nucleotides of 3' splicing sites.

Therefore it is an objective of the present invention to provide a method for determining the presence of introns in eukaroytic genome.

The invention also provides for diagnostic methods employing the characteristic markers of associated introns and exons.

Another objective of the present invention is to provide a method for identification of novel cis- or trans-elements which accurately guide pre-mRNA and alternative splicing.

It is also an objective of the present invention to provide a method for detecting novel introns and exons, therefore, novel mRNA isoforms or protein isoforms.

Yet another objective of the present invention is to provide a method for predicting genes associated with various diseases or genetic mutation based on the splicing junction profile of a given sample of genetic material.

Another objective of the present invention is to provide a method which may be utilized to design DNA/RNA oligomers to detect, identify and screen genetic variations or novel isoforms (DNA, RNA and/or proteins).

It is a further objective of the present invention to provide research and diagnostic methodologies that employ standard laboratory equipment, are relatively inexpensive to perform and which do not require extensive operator skill or training.

Another objective is to provide methods for identifying trans-elements which accurately guide pre-mRNA and alternative splicing.

Various other objectives and advantages of the present invention will become apparent to those skilled in the art as a more detailed description is set forth below.

SUMMARY OF THE INVENTION

The aforementioned and other objectives are realized by providing a method for indirectly detecting introns and exons by determining splice junctions. Specifically, samples are analyzed for the presence of known splicing junctions via comparative genomics, gel electrophoresis or protein chip technologies. If a given sample is found by computational analysis to contain a splice junction, the sample is verified by biochemical experiments for the presence of introns or exons. If an unknown intron or exon is found, it is compared to known mRNAs and ESTs to determine the alteration underlying the disease or genetic mutation. If a given sample is found to contain introns or exons that are not known, the presence of novel introns or exons is likely and can be determined. Thus, the methods herein are applicable for predicting disease or genetic mutations, or for searching for novel introns and exons.

DETAILED DESCRIPTION OF THE INVENTION

Definitions

Figure 1:
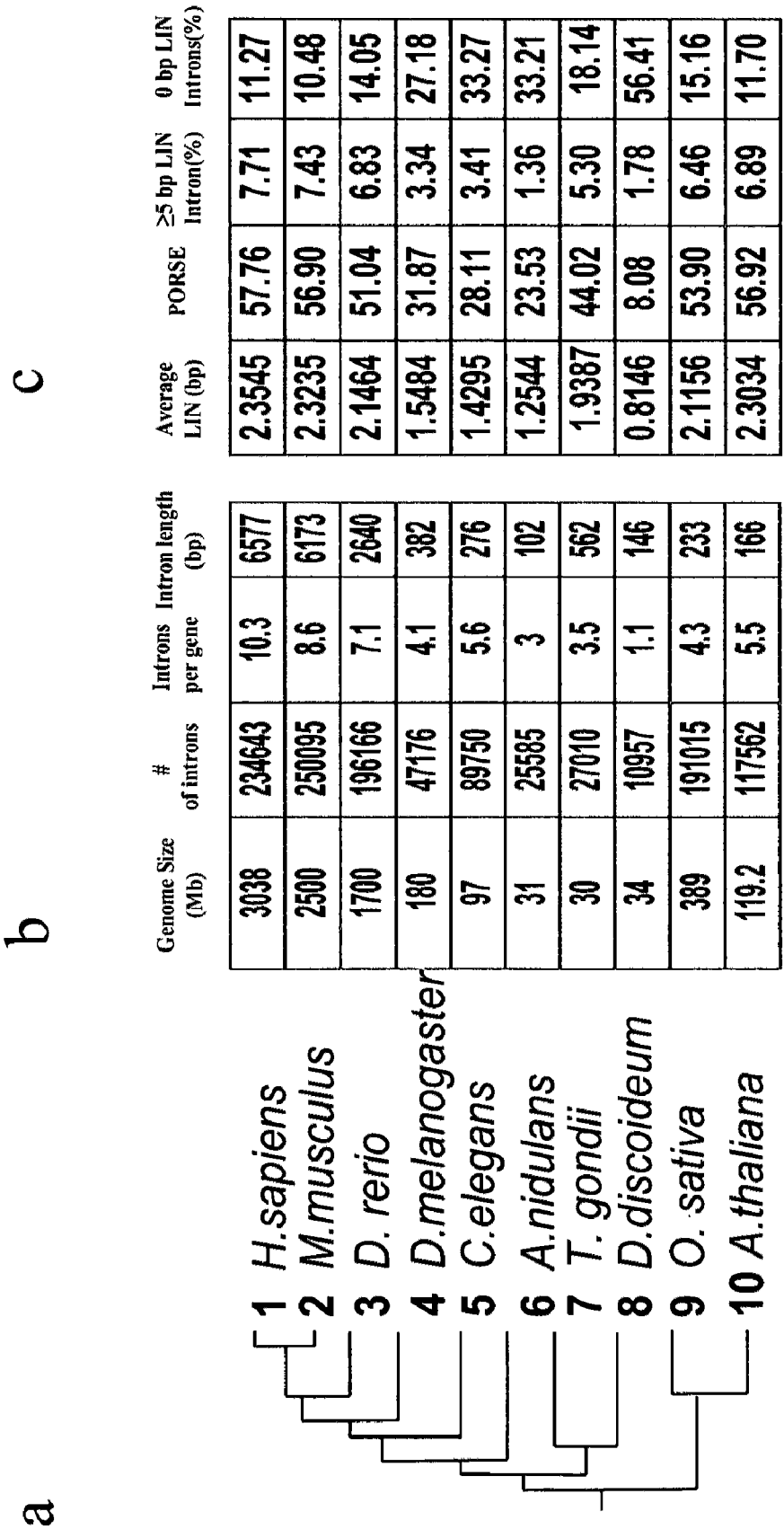
FIG. 1 shows the analysis of LIN (identical lengths of nucleotides) from various organisms. A) Phylogenetic trees of organisms analyzed. B) Basic characteristics of introns from the organisms analyzed. C) Data obtained from our analyses. LIN and PORSE represent the identical lengths of nucleotides and percent overrepresentation (based on randomized sequence expectations, respectively.

The term "intron", as used herein, refers to removed nucleotide sequences from pre-mRNA sequences that were found between 5' and 3' exons. An intron between exons is specifically deemed an "intervening sequence" herein.

The term "splicing junction" used herein generically refers to the site where the breakage in splicing occurs. An intron is further divided into 5' splice site and 3' splice site. 5' splice site were further divided into 5' exonic sequence (E5) and 5' intronic sequences (I5). And 3' splice site was divided into 3' intronic sequences (I3) and 3' exonic sequence (E3) to indicate the end with which they are associated (5' versus 3') and whether the spliced sequences are associated with the exon or intron (E versus I). Here, "splicing junction" is different from "splicing junction region" the latter of which means the splicing junction itself plus adjacent sequences.

"Computational biological methodology" used herein refers to the extraction of useful information from data generated in high-throughput biological techniques, such as gene sequencing. Said methodology employs computerized data sets, software programs for selecting specific data from the data sets and the computers for carrying out the processes.

"Genetic material" used herein generically refers to a purified sample of DNA or RNA. Since mRNA does not contain introns, when "the intron and exons of the genetic material" or a similar statement is made, it is understood that the mRNA may only contain exons.

An "oligomer" herein will refer to a short single strand of DNA.

"Characteristic splicing junction", as used herein, refers to a splicing junction that exhibits the biochemical properties set forth in the present invention. More specifically, a "characteristic splicing junction" will contain either the 20 base pair sequence or 6-15 oligomers described herein.

It is useful to separately describe "Detection of Novel Introns/Exons", "Diagnostic Applications" and "Useful Related Methodology", as set forth below:

Detection of Novel Introns/Exons

Preferred Method of Detecting Novel Introns/Exons (in DNA) or Novel Exons (in mRNA) Using Biological Computational Analysis 1.A) Download genomic sequences and mRNA and EST data from public database, preferably NCBI (ncbi.nlm.nih.gov/Ftp/), but UCSC Genome Browser is also suitable (hgdownload.cse.ucsc.edu/downloads.html). Download genome annotation programs from NCBI, preferably Blast, but Splign and Spidey are also suitable.

2.A) Map mRNA and/or high-quality EST sequence data of a species onto a genome sequence from the corresponding species to identify all putative exon/intron boundaries (splice sites) and all transcription initiation sites and termination sites by Splign or Spidey and Blast programs. Alternatively, download similar genome annotation data of some species (such as human, mouse, *Arabidopsis*) from public databases. The preferred database is GenBank (ncbi.nlm.nih.gov/Ftp/), but AceView is also suitable (ncbi.nlm.nih.gov/IEB/Research/Acembly/downloads.v61.html).

3.A) Parse all high-quality intron data described previously into databases. An intron is divided into a 5' splice site and a 3' splice site. The 5' splice site is further divided into 5' exonic sequence (E5) and 5' intronic sequence (I5) and the 3' splice site into 3' intronic sequence and 3' exonic sequence. Get 50 bp nucleotide sequences from each of E5, I5, I3 and E3 of an intron starting from the splice sites and store the genome-wide information into separate databases.

4.A) Get all gene sequences, index them and store them in a database based on the genome annotation data described in Step 2.

5.A) Several different approaches can be used to identify putative novel introns and exons. To identify all potential alternatively spliced isoforms, one scans an entire gene including all intron sequences, that is, from transcription initiation sites to termination sites, to identify all potential alternative spliced isoforms starting from the first intron. There are three types of alternative splicing (5' alternative splicing, 3' alternative splicing and both 5' and 3' alternative splicing).

6.A) To identify 5' alternatively-spliced isoforms, E5 and I5 sequences of an intron are compared against the remaining sequence to identify whether other sequences are statistically significantly similar to E5 and I5 sequences at nucleotide levels and/or amino acid levels. Statistically significant sequences are 50% and above. If a region is similar to E5 and I5 sequence with GT or GC nucleotides, this is a 5' alternatively-spliced isoform with the intron beginning GT or GC.

7.A) To identify 3' alternatively-spliced isoforms, I3 and E3 sequences of an intron are compared against the remaining sequence to identify whether other sequences are statistically significantly similar to I3 and E3 sequences at nucleotide levels and/or amino acid levels. If a region is similar to I3 and E3 sequence containing AG dinucleotide, this is a 5' alternatively-spliced isoform with the intron ending AG.

8.A) To identify both 5' and 3' alternatively-spliced isoforms, E5 and I5 sequences which have both GT or GC and/or AG are compared against the remaining sequence to identify whether other sequences are statistically significantly similar to I3 and E3 sequences at nucleotide levels and/or amino acid levels. If the region contains multiple ($\geq 3$) E5-I5 sequences, this region potentially has one or more 5' and 3' alternatively-spliced isoforms, as well as 5' or 3' alternatively-spliced isoforms.

9.A) Special attention should be paid to transposable or retroposon elements, since they usually generate multiple alternatively-spliced isoforms when these elements are clustered together.

10.A) Another method of detecting alternatively-spliced intron, is to correlate six nucleotides (hexamer) located within a splice junction with one of the first six nucleotides of all I5 sequences from the database described in Step 3. An alternatively-spliced intron is detected if the following conditions are met: A) an eight nucleotide sequence (E5) exists immediately upstream of these hexamers; B) eight nucleotides ending with AG (I3) are identical to those eight nucleotides (E5); and C) eight nucleotides (I3) are identical to those introns from the all intron dataset. The sequences from I5 beginning GT to I3 ending AG is a novel intron, the sequence upstream and downstream are 5' exon and 3' exon respectively.

Preferred Method of Detecting Novel Introns/Exons (in DNA) or Novel Exons (in mRNA) Using Gel Electrophoresis (and Computational Analysis)

1.B) Identify potential novel isoforms by computational methods as described previously.

2.B) Using conventional laboratory procedures, isolate total RNAs or mRNAs from various tissues (such as eyes, muscles, lungs and livers) and/or cell lines (such as stem cells) and/or different developmental stages (such as 2 day embryos, 15 day embryos and adults) from the corresponding species.

3.B) Synthesize cDNAs from RNAs of various sources described previously after the RNAs are treated by RNase-free DNase to remove DNAs. Preferred method of cDNA synthesis is reversed transcription by olig(dT)$_n$, but employing randon hexamers is also suitable. The preferred RNase-free DNase is sold under the name RNase-free DnaseI by New England Biolabs of USA.

4.B) Design forward primers in putative 5' exons predicted previously and reverse primers in putative 3' exons. Designing primers is preferably facilitated by PRIMER3 program (version 0.4.0) produced by Steve Rozen and Helen J, Skaletsky of Whitehead Institute, Cambridge, Mass. If the pre-mRNA contains multiple repeat regions, design forward primers and reverse primers outside these repeat regions.

5.B) Amplify the cDNAs using the forward and reverse primers. Amplification is preferably performed by RT-PCR.

6.B) Separate the PCR products on agarose gel by electrophoresis. This is the preferred method. Alternatively, PCR products may be separated on RNA chips by Caliper 90 (Caliper Life Sciences, Hopkinton, Mass.) to assess their size. Using conventional techniques, check the gel or chips for expected PCR products by size.

7.B) Clone and sequence the PCR products, preferably using the TA Cloning or Topo TA Cloning by Introgene.

8.B) Align the sequences from these products with the genomic sequences by programs such as Blast, Blat (developed by W. J Kent of UCSC), Splign or Splidey to verify whether or not these products are novel isoforms. A novel isoform is defined as mRNA sequences different from the reference mRNA sequences. The preferred program is Splign or Splidey.

9.B) Investigate that the novel isoforms are expressed at developmental stages, including mouse one-cell stage embryo (fertilised egg), blastocyst (zona pellucida absent) and differentiation of egg cylinder, tissues including eyes, muscles, lungs and livers, and cell types including human Mantle cell lymphoma and B-prolymphocytic leukemia (B-PLL) by RT-PCR and Northern blot hybridization. Specifically, confirmation is determined by real-time PCRs.

Preferred Method of Detecting Novel Introns/Exons (in DNA) or Novel Exons (in mRNA) Using DNA Chips (and Computational Analysis)

1.C) Identify potential novel isoforms by computational methods as described previously in Steps 1A-10A.

2.C) Isolate total RNAs or mRNAs from various tissues and/or cell lines and/or different developmental stages from the corresponding species.

3.C) Design set of oligos ranging from 18-80 bp (or DNA fragments) based on the junction sequence of predicted E5 and E3 sequences. Design oligos from the E5 and E3 sequences as controls. Oligos are preferably designed by Primer 3.

4.C) These oligos are applied generally onto glass or nylon substrates by high-speed robotics to fabricate DNA chips. The preferred substrate is glass. The oligos are used to determine complementary binding, which facilitates parallel study of predicted alternatively-spliced isoforms.

5.C) Hybridize DNA chips with cDNAs or RNAs from various sources such as different persons, different tissues, different developmental stages and different cells or cell lines.

6.C) Analyze DNA hybridization data from DNA chips to verify these novel alternatively-spliced isoforms. Verification is indicated by RT-PCR.

7.C) Confirm that the novel isoforms are expressed at developmental stages, tissues and cell types by RT-PCR, Northern blot hybridization or DNA chips.

8.C) Not all of these predicted isoforms can be easily detected because low levels of gene expression (for example isoforms of insulin receptors), tissue-specificities (for example one of the platelet activating factor acetylhydrolase isoforms is expressed exclusively in testis), expression at certain developmental stages (for example the TFoxK1 splice variants were differentially expressed between fast and slow myotomal muscle of adult fish while the FoxK1-alpha protein was expressed in myogenic progenitor cells of fast myotomal muscle) or cell types (for example Endothelin-converting enzyme-1d is the most abundant type in several endothelial cells (EC) types).

9.C) Collect all confirmed novel isoforms into database.

Diagnostic Applications

The diagnostic applications are based on the fundamental similar 5' and 3' splicing junctions which originated and evolved from the sequences which correlate with specific known exons and introns, and these specific known exons and introns correlate with specific genetic mutations and diseases. Thus, one means to screen for or diagnose specific conditions is to analyze a sample of genetic material to determine whether or not it contains characteristic splicing junctions.

Preferred Method of Diagnosing Disease Using Biological Computational Analysis

1.D) Identify novel isoforms dataset as described from previous sections.

2.D) Download SNPs and haplotypes from public databases. The preferred SNPs download database is found at NCBI. The preferred human haplotype download database is found on the internet at the hapmap.org website.

3.D) Analyze these data to identify genetic variations that abolish or increase gene expression of novel alternatively-spliced isoforms. Identification of variations that abolish gene expression of novel alternatively-spliced isoforms is performed by RT-PCR and DNA chips. Identification of variations that increase gene expression of novel alternatively-spliced isoform is preferably performed by RT-PCR and DNA chips in conjunction with real-time PCR.

4.D) The SNPs and haplotype data are used to study whether diseases or phenotypes are associated with these genetic variations by linkage disequilibrium (LD), the long-range haplotype (LRH) and the integrated haplotype score (iHS). Specifically, LD is characterized by the non-random association of alleles at two or more loci, not necessarily on the same chromosome. LRH is characterized by long-range linkage disequilibrium (LD), which suggest the haplotype rapidly rose to high frequency before recombination could break down associations with nearby markers. iHS is characterized by statistical analysis known in the art which has been developed to detect evidence of recent positive selection at a locus and based on the differential levels of linkage disequilibrium (LD) surrounding a positively selected allele compared to the background allele at the same position.

5.D) These data are also used to study whether diseases or phenotypes are caused by these genetic variations via case-control association study, which are well known in the art.

Preferred Method of Diagnosing Disease Using Gel Electrophoresis (and Computational Analysis)

1.E) Identify novel isoforms dataset as described in the previous sections.

2.E) Download SNPs and haplotypes from public databases as described above.

3.E) Sequence genomic regions of interest to verify genetic variations from public databases such as OMIM, Online Mendelian Inheritance in Man or Online Mendelian Inheritance in Animals. A genomic region of interest is defined as nucleotide variations affecting pre-mRNA splicing. Genetic variation is verified against a normal reference standard.

4.E) Verify the genetic variations that alter alternatively-spliced isoforms by RT-PCR and/or Northern blot analysis. The preferred method is TagMan real-time RT-PCR, which is performed and verified by conventional protocol of Applied Biosystems.

5.E) For the repeat elements, which are characterized as sequence similarities, forward primers and reverse primers are designed based on the sequences out of the repeat region, for example, on different exons. These primers are used to amplify the targeted region by RT-PCR according to standard procedures.

6.E) The PCR products are separated on agarose gels or RNA chips. The RT-PCR products with different sizes are further sequenced to identify the repeat elements. Repeat elements are defined as regions sharing similar sequences.

7.E) Collect data from normal and disease groups to analyze statistically whether these genetic variations are associated with the diseases. For examples, samples of human blood are collected from different groups of people (for example healthy versus cancer patients), and those samples are analyzed according to genotyping. Genetic variations and disease are considered statistically significant where P <0.05.

Preferred Method of Diagnosing Disease Using DNA Chips (and Computational Analysis)

1.F) Identify novel isoforms dataset as described from the previous sections.

2.F) Download SNPs and haplotypes from public databases as previously described.

3.F) Design set of oligos ranging from 18-80 bp (or DNA fragments) based on the junction sequence of predicted E5 and E3 sequences as well as E5, I5, I3 and E3 sequences. The E5 and E3 predictions are by our prediction based on splicing junctions. Design oligos from the E5 and E3 sequences as positive controls with the oligos from I5 and I3 as negative control. Oligos are preferably designed by Primer 3.

4.F) These oligos are applied generally onto glass or nylon substrates by high-speed robotics to fabricate DNA chips. The oligos are used to determine complementary binding, thus allowing a massively parallel study of predicated alternatively-spliced isoforms. This is described in greater detail above.

5.F) Hybridize DNA chips with cDNAs or RNAs from individuals of normal and diseases groups according to methods well known in the art.

6.F) Identify alternation of copy numbers of repeat elements and changes in gene expression of novel alternatively-spliced isoforms. Alternation of novel alternatively-spliced isoforms is characterized by different levels. Changes in expression of novel alternatively-spliced isoforms is characterized by different patterns. Preferably, RT-PCR and DNA sequencing are used to verify the results from DNA chips, with 100% sequence dientities considered verification.

7.F) Analyze statistically the data from DNA chips to identify which genetic alternations will be associated with diseases. Analysis is preferably performed by real-time RT-PCR. Statistical significance is considered against the control at p<0.01.

Useful Related Methodology

Preferred Method of Identifying Trans-Elements which Accurately Guide Pre-mRNA and Alternative Splicing 1) Since these trans-acting elements regulate pre-mRNA splicing and alternative splicing via specific base-paring interaction with the 5' exonic (E5) and intronic nucleotide sequences (I3), these elements can be RNA molecules or proteins.
2) If these elements are RNAs, first get and verify the 5' exonic nucleotide sequences (E5), 3' intronic nucleotide sequences (I3).
3) Starting from the 5' splice junction, the last nucleotide (−1) of the 5' exon will be complementary to a nucleotide of the elements (G-C, A-T, C-G, T-A), then the last second nucleotide (−2) of the 5' exons complementary to the next nucleotide of the elements (G-C, A-T, C-G, T-A) in 5'->3' direction. And so on, the base-paring interaction between two molecules is up to 10 bp length.
4) Starting from the 3' splice junction, the last nucleotide (−1) of the intron will be complementary to a nucleotide of the elements (G-C, A-T, C-G, T-A), then the last second nucleotide (−2) of the intron complementary to the next nucleotide of the elements (G-C, A-T, C-G, T-A) in 5'->3' direction. And so on, the base-paring interaction between two molecules is up to 10 bp length.
5) The element may be one RNA molecule interacted with both 5' exonic sequence and 3' intronic sequences. They may be located on two different RNA molecules.
6) The trans-acting RNAs may also contain elements that interact with other components of spliceosome.
7) If the elements are protein molecules, one can use the last ten nucleotide sequences of 5' exon or intron as baits to bind the proteins.
8) Extract nuclear proteins from nucleus.
9) Label E5 or I3 ribonucleotide ologi with $^{32}P$
10) Incubate E5 or I3 oligo with protein extracts in presence of no-specific DNAs.
11) Separate the protein-oligo mix on polyacrymide gels.
12) Purify the proteins that specifically interact with E5 or I3 oligo.
13) Sequence the purified protein.
14) Get gene sequence from the protein sequences.
5) Characterize the gene functions by siRNA.

For purposes of illustration, the following Experimental Findings and Experimental Methods are set forth. These Findings and Methods were originally published in "Modern origin of numerous alternatively spliced human introns from tandem arrays" Proc Natl Acad Sci USA. 2007 Jan. 16; 104 (3):882-6. Epub 2007 Jan. 8, which is incorporated herein:

Experimental Findings

Evolutionary young intron data sets were searched for by identifying very similar sequences at the 5' and 3' splice junctions. Such a pattern could result from recent tandem segmental duplication of pre-existing genic (or flanking sequences) or from direct repeats generated during transposition (or possessed by TEs). In this way, human introns with long LIN (length of identical nucleotides) were identified, and a subset of them appears to have originated after the human-chimpanzee split (about 5 million years ago).

Figure 7:
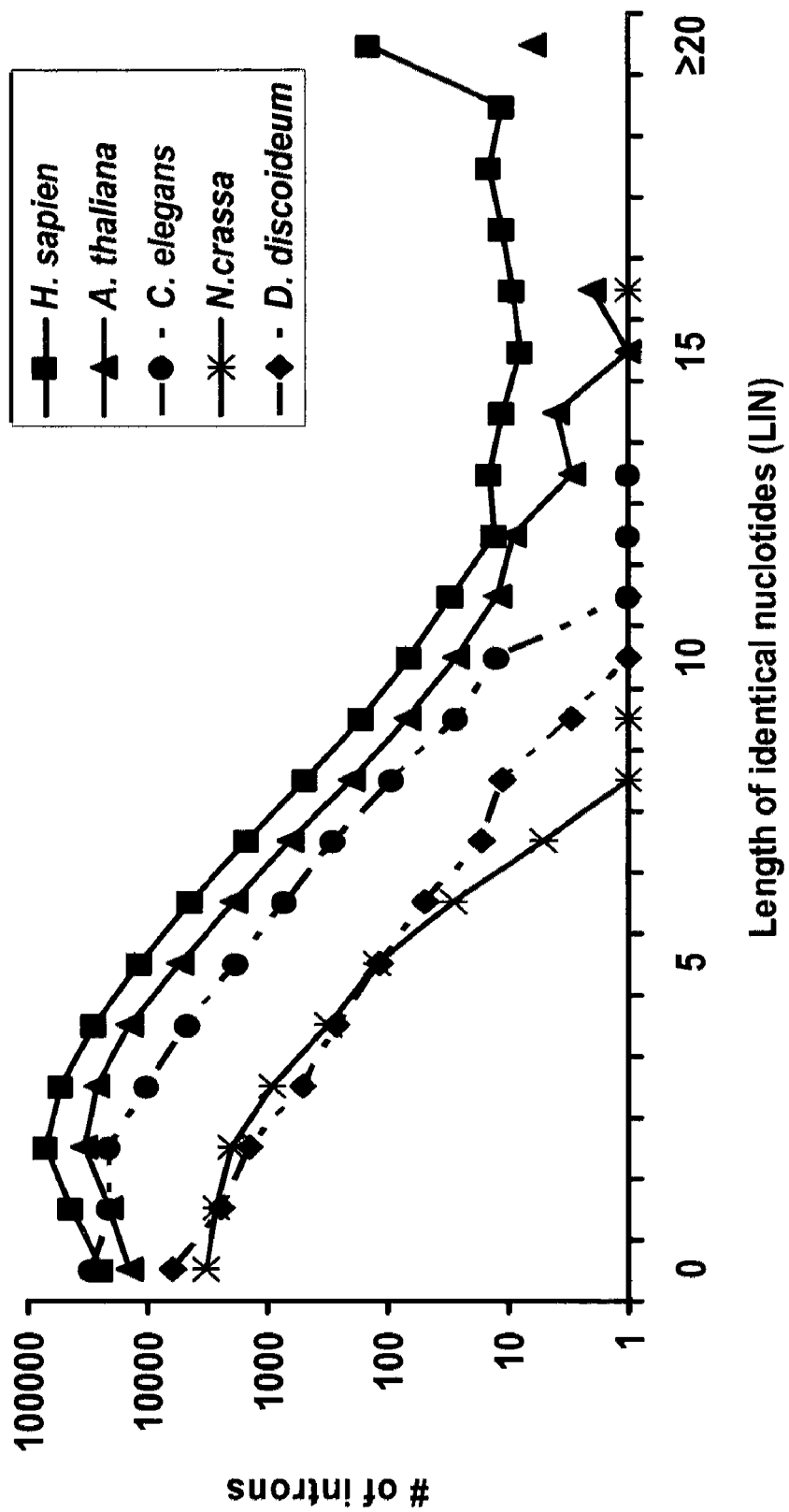
FIG. 7 shows the comparative analysis of LIN distribution from various intron datasets from different organisms including human a) human, *Arabidopsis*, zebrafish, *D. melanogaster, C. elegans,* and *D.discoideum.*
Figure 8:
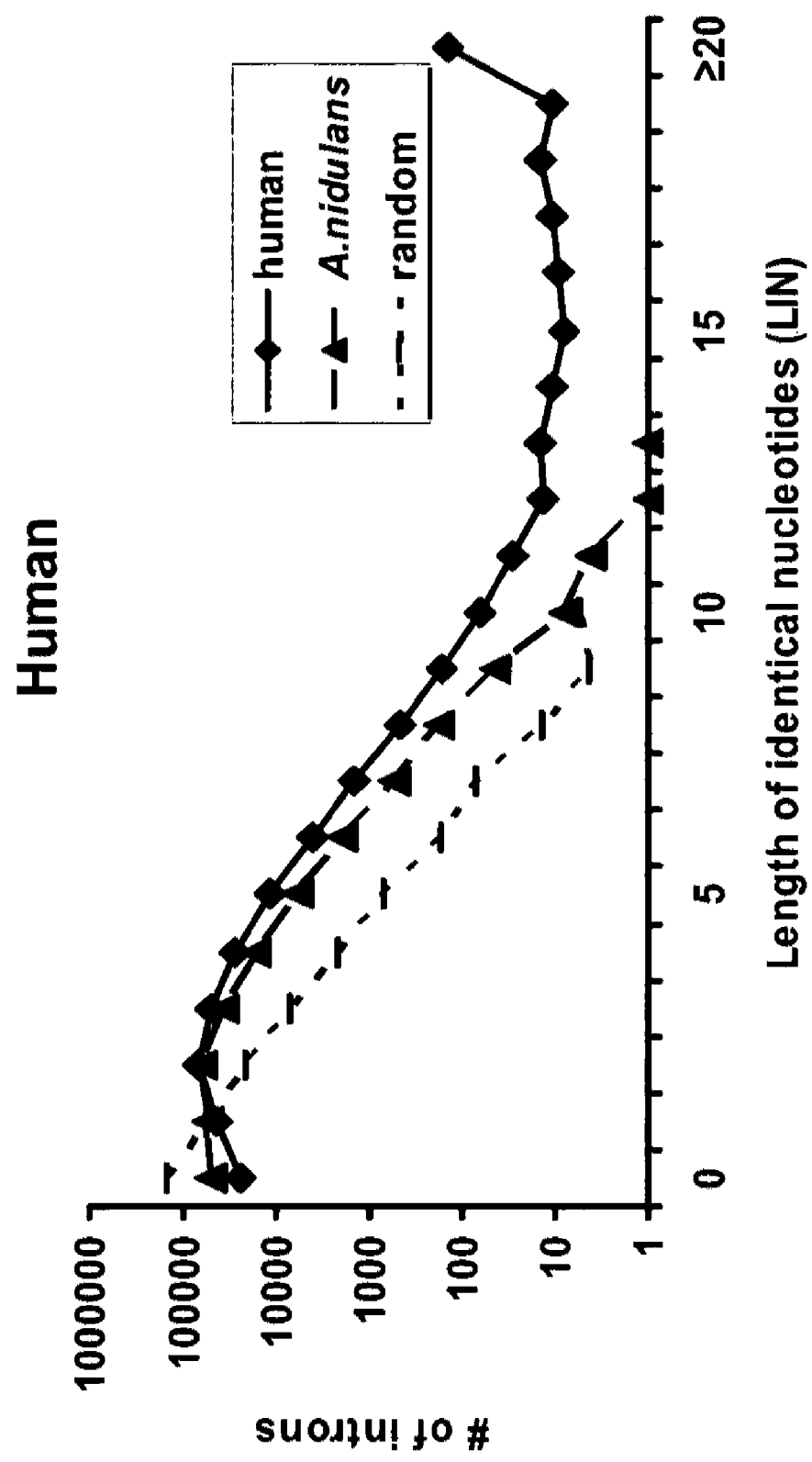
FIG. 8 shows the analysis of the different LIN distribution from the total human introns (solid lines). The random sequences (lines) and *Aspergillus nidulans* introns (triangles) were used as controls.
Figure 9:
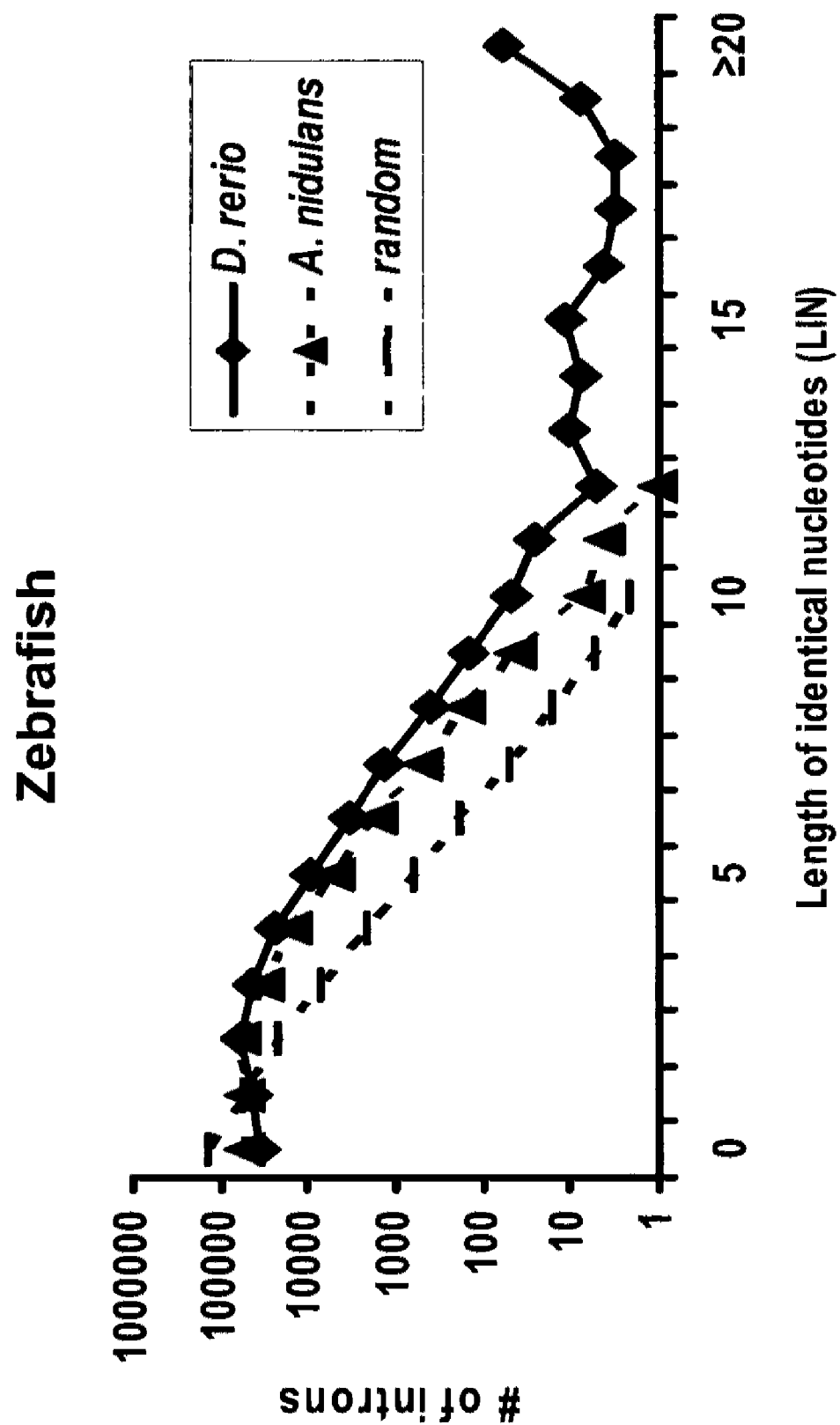
FIG. 9 shows the analysis of the different LIN distribution from the total zebrafish intron dataset (solid lines). The random sequences (lines) and *Aspergillus nidulans* introns (triangles) were used as controls.
Figure 10:
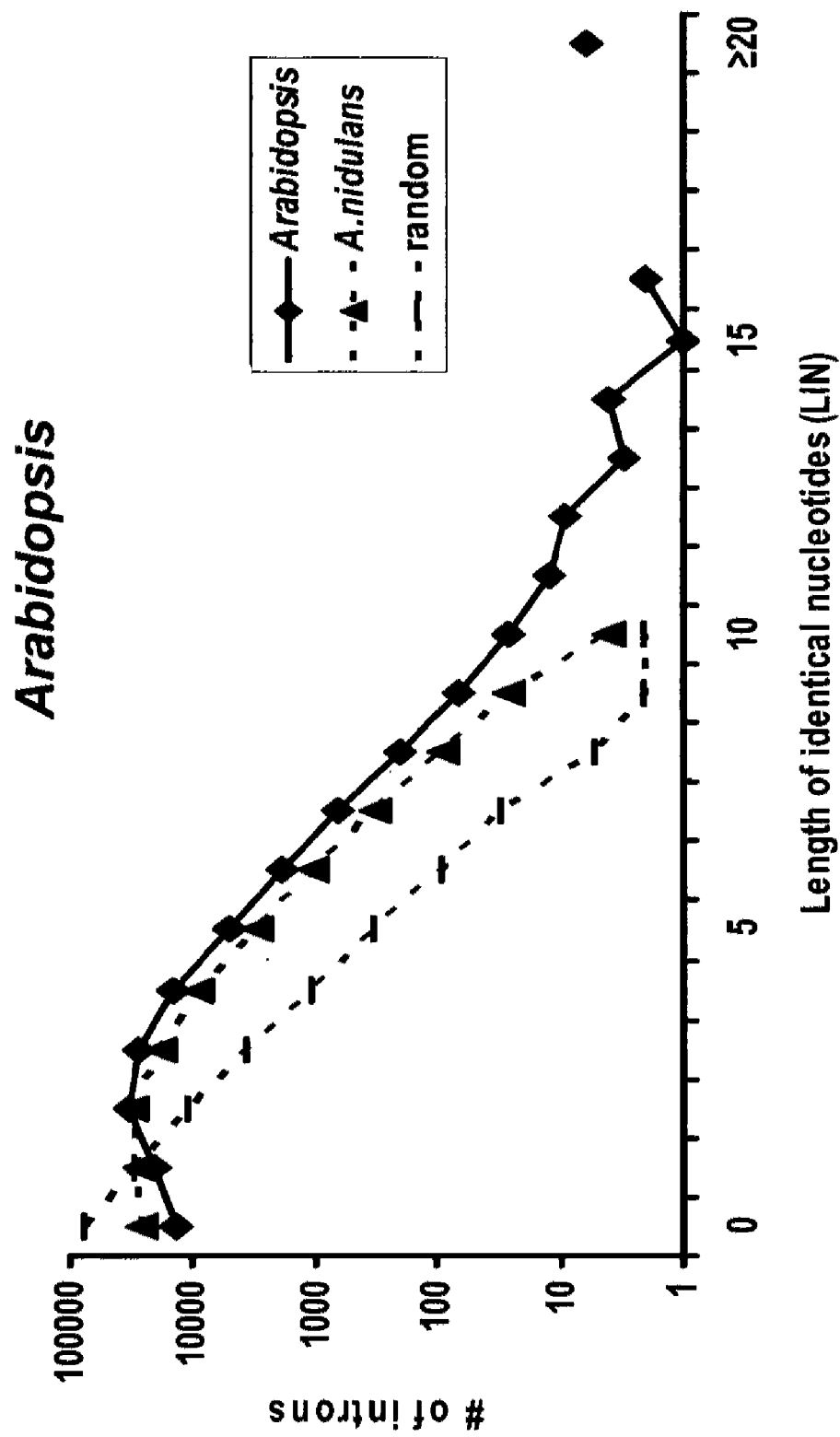
FIG. 10 shows the analysis of the different LIN distribution from the total *Arabidopsis* introns (solid lines). The random sequences (lines) and *Aspergillus nidulans* introns (triangles) were used as controls.
Figure 11:
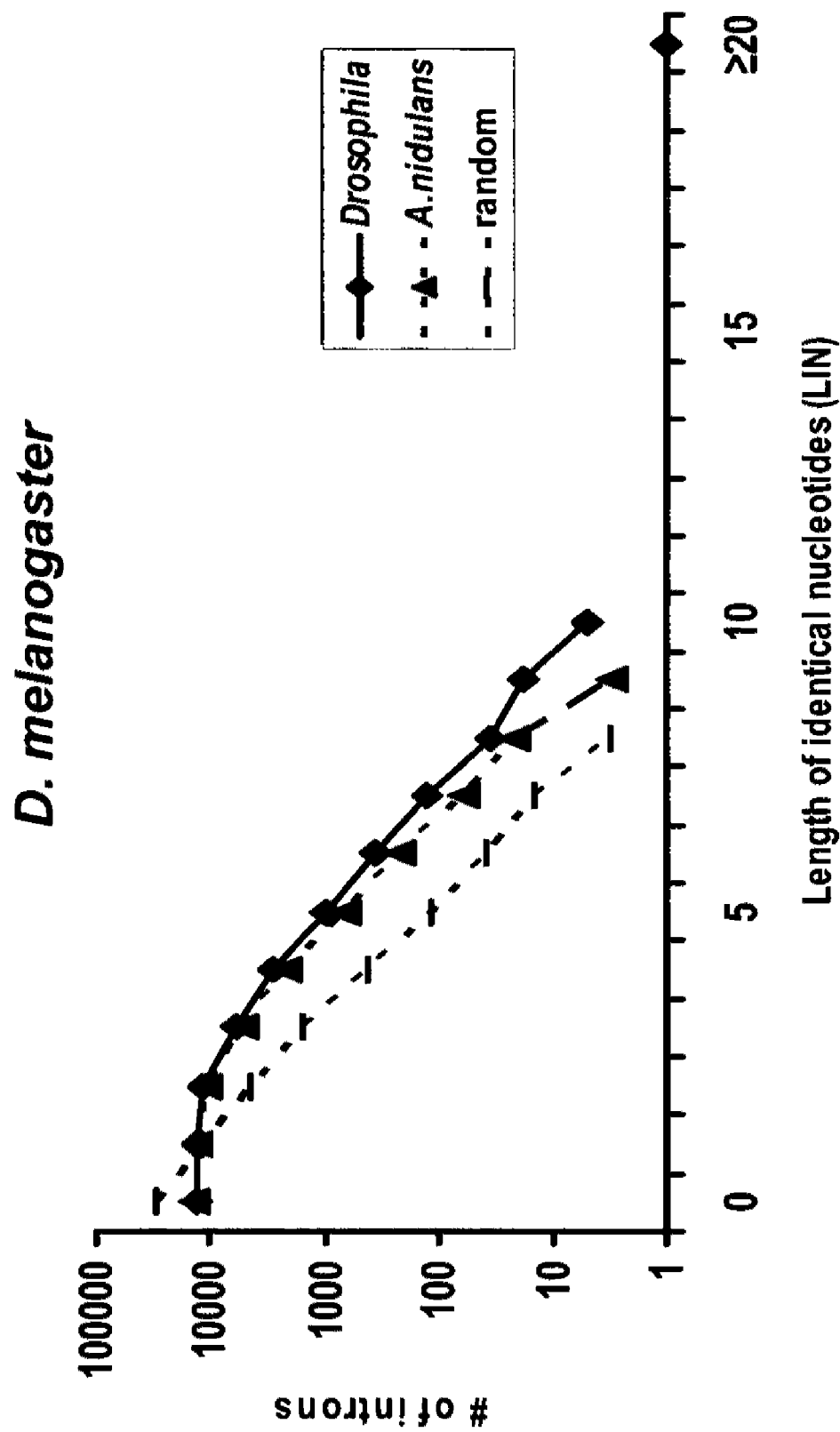
FIG. 11 shows the analysis of the different LIN distribution from the total *D. melanogaster* introns (solid lines). The random sequences (lines) and *Aspergillus nidulans* introns (triangles) were used as controls.
Figure 12:
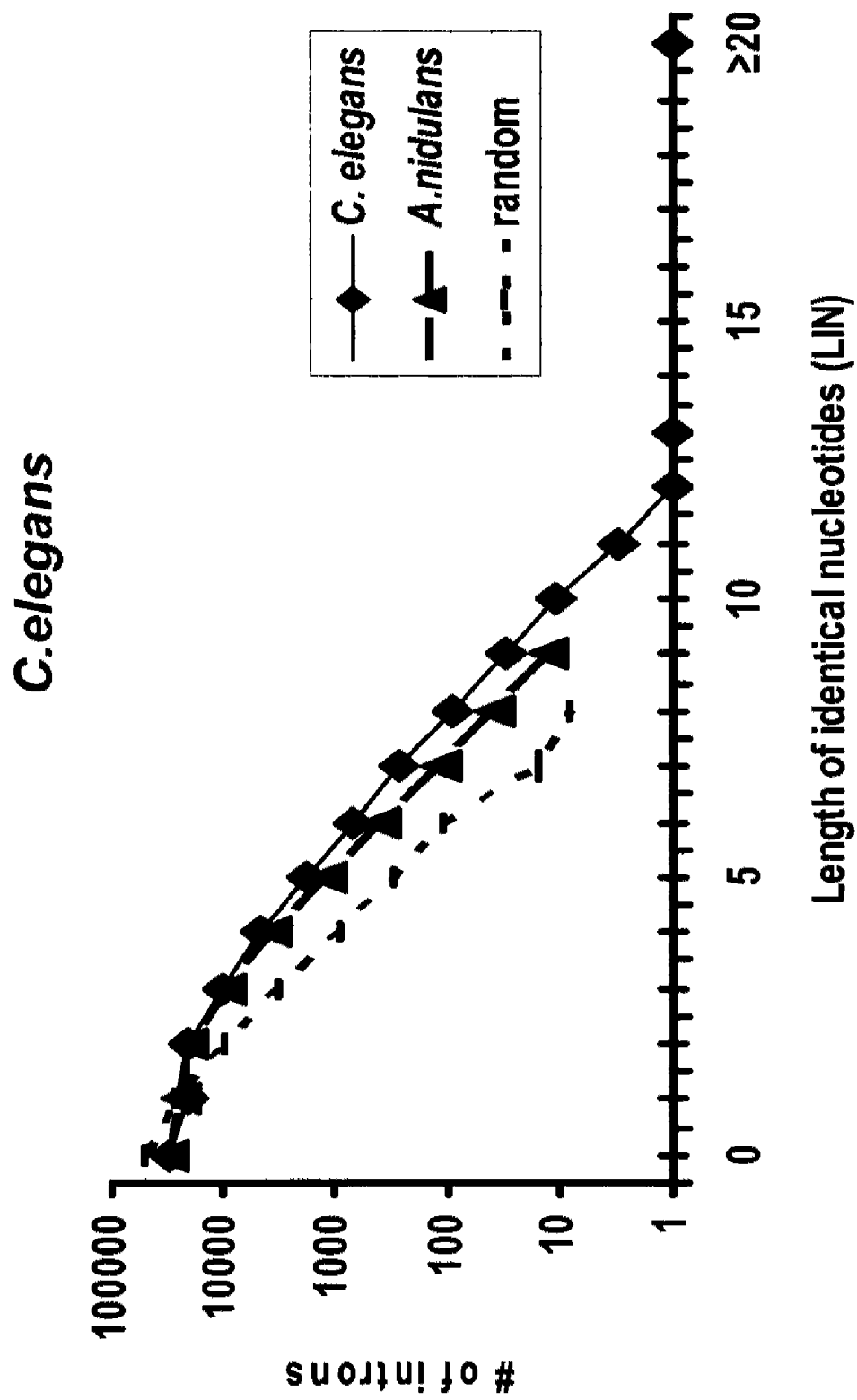
FIG. 12 shows the analysis of the different LIN distribution from the total *C. elegans* introns (solid lines). The random sequences (lines) and *Aspergillus nidulans* introns (triangles) were used as controls.
Figure 13:
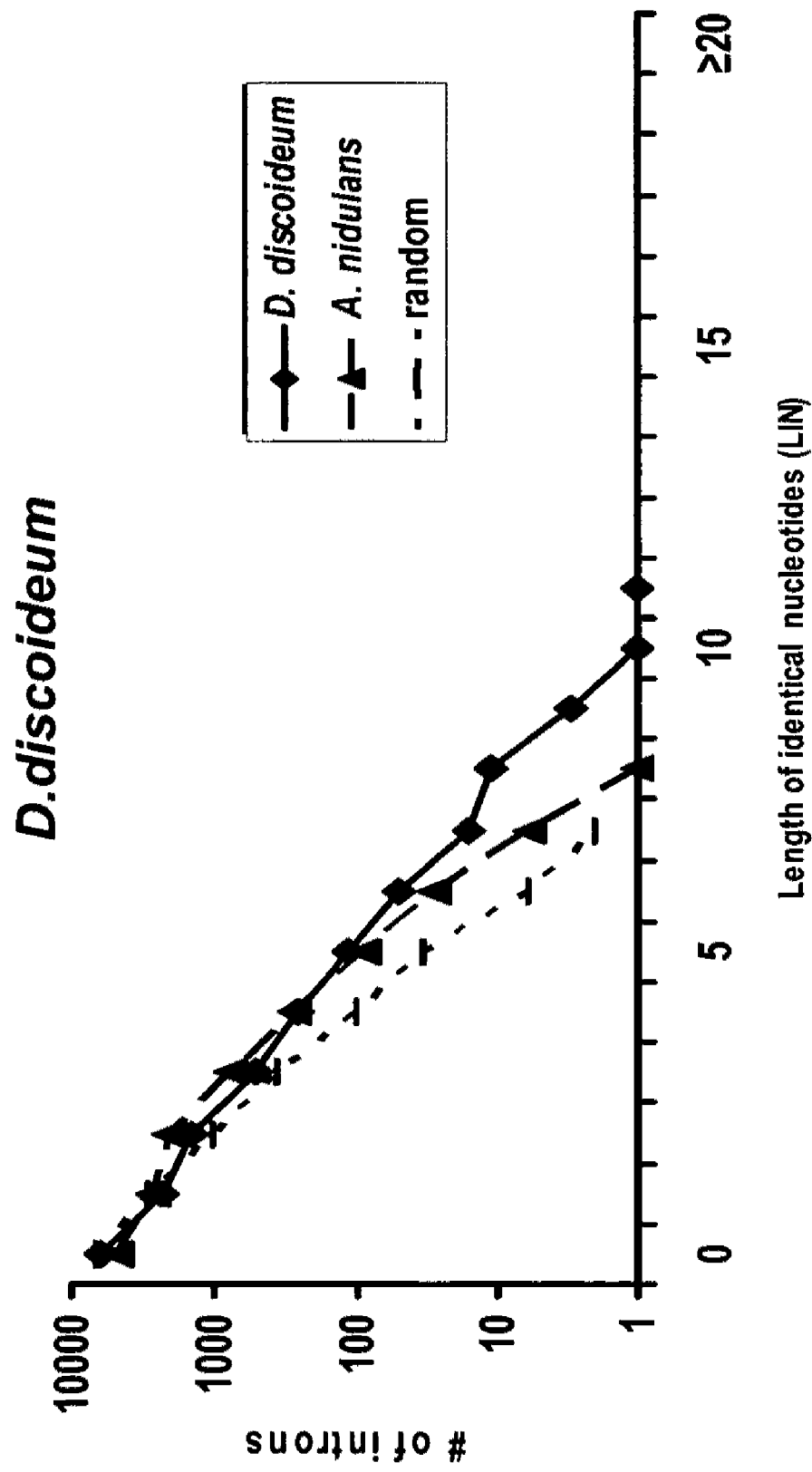
FIG. 13 shows the analysis of the different LIN distribution from the total *D. discoideum* introns (solid lines). The random sequences (lines) and *Aspergillus nidulans* introns (triangles) were used as controls.
Figure 14:
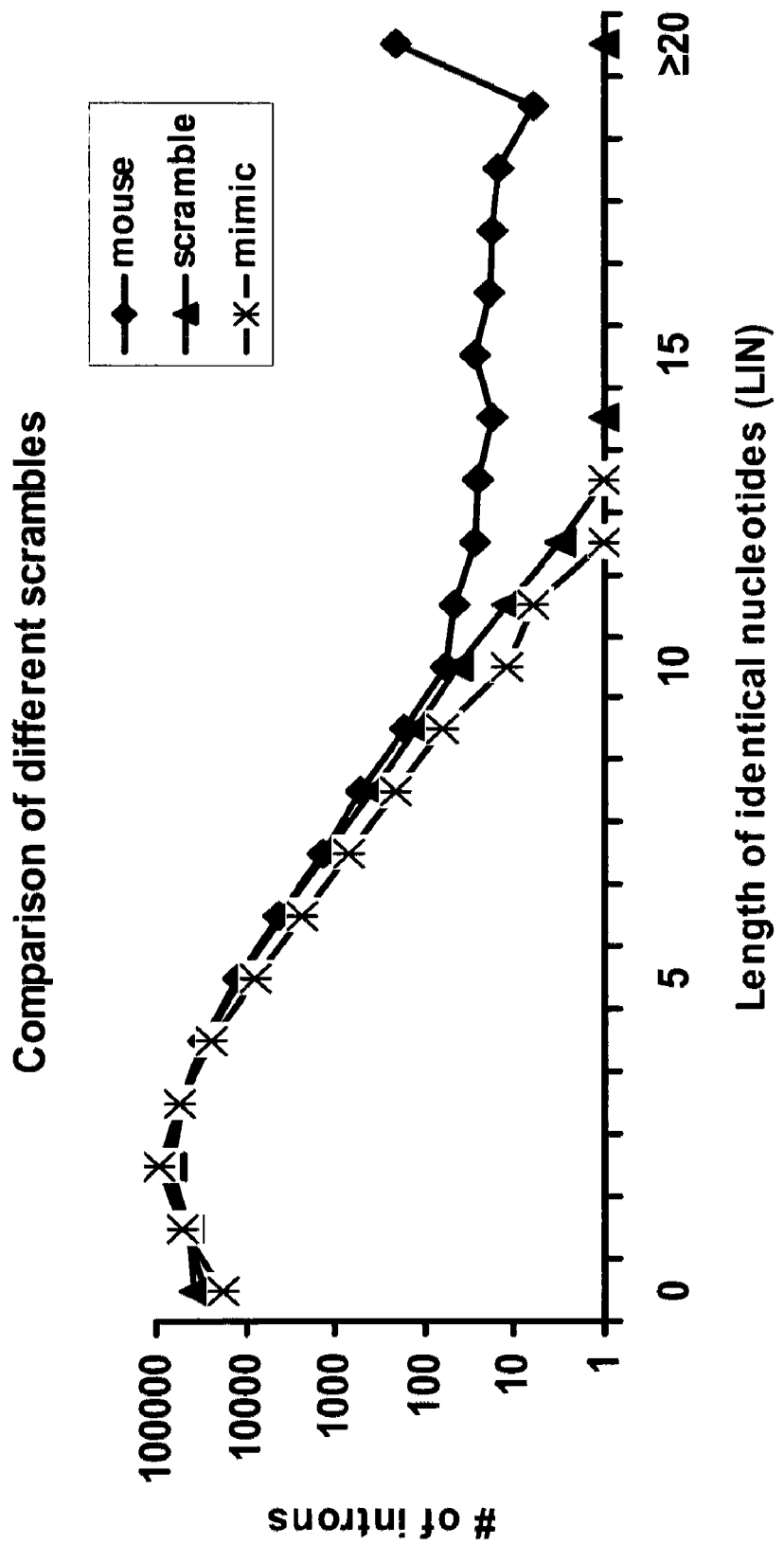
FIG. 14 shows a comparison between different scrambles. Scramble is that E5, I5, I3 and E3 of a mouse intron that are randomly mix-and-matched with I3, E3, E5 and I5 of an intron randomly selected from the mouse intron dataset. Mimic represents that E5, I5, I3 and E3 of a mouse intron that are randomly scrambled with I3, E3, E5 and I5 of randomly selected *A. nidulans* intron whose dataset is mimic GT-AG frequency of the mouse intron dataset.

To determine whether short segmental duplications may be playing a widespread role in intron creation in other eukaryotic lineages, intron datasets for diverse vertebrates (mouse, human, zebrafish), invertebrates (*Drosophila melanogaster, C. elegans*), fungi (*Aspergillus nidulans*), protists (Dictylostelium, Toxoplasma) and plants (rice, *Arabidopsis*) were generated as described in the Experimental Methods section. FIG. 1 shows the evolutionary tree. Intron/exon junctions were scored with respect to length of identical nucleotides (LIN) observed between the 5' splice junction (designated as E5 and I5) and the 3' splice junction (designated as I3 and E3), shown in FIG. 2. It is worth noting that by including only those with complete identity, cases of high similarity (albeit less than 100%) are excluded from the analysis. In the example shown in FIG. 1, mouse intron 10 of 1827 bp in Tbc1d2 shows a total of 9 identical nucleotides (namely six between E5 and I3 and three between I5 and E3). Plots of the numbers of introns found for LIN varying from 0 to 20 for mouse, rice, *Aspergillus*, Toxoplasma are shown in FIGS. 3-6, respectively and a composite plot for human, zebrafish, *Arabidopsis, C. elegans, D. melonogaster* and *D. discoideum* is shown in FIG. 7. Individual plots for the others are shown as FIGS. 8-13. For mouse, rice and Toxoplasma there are many introns of LIN $\geq 10$. To assess whether these numbers are indeed larger than predicted by random chances, mouse introns were compared against the mouse scramble and mimic scramble (*Aspergillus nidulans* introns whose GT-AG frequency equivalent to that of mouse introns) as well as a random intron scramble using the fungal *Aspergillus nidulans* intron dataset (mixed with that of the organism of interest). As FIG. 14 and Table 1 show, mouse introns with LIN $\geq 5$ are 7% to 45 fold higher than the all controls (U-test, p<0.001) and the scramble control has more LIN $\geq 5$ introns than the mimic one, suggesting the many mouse intron splicing junctions are redundant. To avoid distorting analysis by a few genes as seen in *Drosophila* Dscam, *A. nidulans* was chosen as control because it is rather distantly related to both plants and animals (although a sister Glade of animals) and its intron density is similar to that of insects and fishes, in contrast to many other fungi or protists. Most importantly, it lacks the confounding redundancy seen for complex genomes like the human one. Additional statistical support for the significant nature of the excess in introns with long identical splice junctions is given as Table 2.

est average LIN. 56% of the introns have LIN 0 and only 1.8% of the dataset have LIN≧5 bp. Possible explanations are that these introns are old (so that similarities have eroded away) or different mechanisms of origin, or impact of very high AT content in these genomes. Moreover, introns are very variable and sometimes very short. The majority of the LIN8 bp introns (namely 16) in *D. discoideum* show long homopolymeric stretches of A in these A-T rich genes. On the other

TABLE 1

| LIN | Mouse | Scramble | Mimic | *A. nidulans* | Mouse/Scramble | Probability | Mouse/Mimic | Probability | Mouse/*A. nidulans* | Probability |
|---|---|---|---|---|---|---|---|---|---|---|
| 0 | 28175 | 38725 | 18017 | 56421 | 0.73 | $p < 0.001$ | 1.56 | $p < 0.001$ | 0.50 | $p < 0.001$ |
| 1 | 46039 | 44270 | 48950 | 59571 | 1.04 | $p < 0.001$ | 0.94 | $p < 0.001$ | 0.77 | $p < 0.001$ |
| 2 | 73307 | 68684 | 93570 | 67506 | 1.07 | $p < 0.001$ | 0.78 | $p < 0.001$ | 1.09 | $p < 0.001$ |
| 3 | 54789 | 52733 | 55246 | 39233 | 1.04 | $p < 0.001$ | 0.99 | $p < 0.5$ | 1.40 | $p < 0.001$ |
| 4 | 29000 | 28703 | 23288 | 17989 | 1.01 | $p < 0.5$ | 1.25 | $p < 0.001$ | 1.61 | $p < 0.001$ |
| 5 | 11983 | 11219 | 7648 | 6383 | 1.07 | $p < 0.001$ | 1.57 | $p < 0.001$ | 1.88 | $p < 0.001$ |
| 6 | 4254 | 3938 | 2363 | 2127 | 1.08 | $p < 0.001$ | 1.80 | $p < 0.001$ | 2.00 | $p < 0.001$ |
| 7 | 1408 | 1247 | 721 | 608 | 1.13 | $p < 0.001$ | 1.95 | $p < 0.001$ | 2.32 | $p < 0.001$ |
| 8 | 504 | 391 | 211 | 185 | 1.29 | $p < 0.001$ | 2.39 | $p < 0.001$ | 2.72 | $p < 0.001$ |
| 9 | 170 | 123 | 61 | 58 | 1.38 | $p < 0.001$ | 2.79 | $p < 0.001$ | 2.93 | $p < 0.001$ |
| 10 | 59 | 44 | 12 | 13 | 1.34 | $p < 0.5$ | 4.92 | $p < 0.001$ | 4.54 | $p < 0.001$ |
| 11 | 46 | 12 | 6 | 1 | 3.83 | $p < 0.001$ | 7.67 | $p < 0.001$ | 46 | $p < 0.001$ |
| 12 | 28 | 3 | 1 | | 9.33 | $p < 0.001$ | 28 | $p < 0.001$ | ∞ | $p < 0.001$ |
| 13 | 25 | 1 | 1 | | 25 | $p < 0.001$ | 25 | $p < 0.001$ | ∞ | $p < 0.001$ |
| 14 | 18 | 1 | | | 18 | $p < 0.001$ | ∞ | $p < 0.001$ | ∞ | $p < 0.001$ |
| 15 | 27 | | | | ∞ | $p < 0.001$ | ∞ | $p < 0.001$ | ∞ | $p < 0.001$ |
| 16 | 19 | | | | ∞ | $p < 0.001$ | ∞ | $p < 0.001$ | ∞ | $p < 0.001$ |
| 17 | 17 | | | | ∞ | $p < 0.001$ | ∞ | $p < 0.001$ | ∞ | $p < 0.001$ |
| 18 | 15 | | | | ∞ | $p < 0.001$ | ∞ | $p < 0.001$ | ∞ | $p < 0.001$ |
| 19 | 6 | | | | ∞ | $p < 0.05$ | ∞ | $p < 0.05$ | ∞ | $p < 0.05$ |
| ≧20 | 206 | 1 | | | 206 | $p < 0.001$ | ∞ | $p < 0.001$ | ∞ | $p < 0.001$ |

TABLE 2

Introns (LIN ≧ 6)

| Species | Observed | Scramble | Observed/Scramble | Probabilities (p) |
|---|---|---|---|---|
| Human | 6703 | 2119 | 3.2 | $p < 0.001$ |
| Mouse | 6802 | 2992 | 2.3 | $p < 0.001$ |
| zebrafish | 5517 | 2472 | 2.2 | $p < 0.001$ |
| *D. melangaster* | 558 | 316 | 1.8 | $p < 0.001$ |
| *C. elegans* | 1091 | 232 | 4.7 | $p < 0.001$ |
| *A. nidulans* | 100 | 99 | 1.0 | $0.5 < p < 0.677$ |
| *T.gondii* | 490 | 213 | 2.3 | $p < 0.001$ |
| *D. discoindeum* | 81 | 35 | 2.3 | $p < 0.001$ |
| rice | 4230 | 2119 | 2.0 | $p < 0.001$ |
| *A. thaliana* | 2914 | 1467 | 2.0 | $p < 0.001$ |

For mouse introns, 7.5% fall in the category of having LIN≧5, and 6.5% for rice with absolute numbers of 18785 and 12317, respectively and for ≧20 LIN there were 206 and 15 respectively. Notably plant introns are on average also much shorter. The mammal/plant value is about 5-fold higher than for fungi (See FIG. 1). Indeed, for *Aspergillus*, there are no LIN≧10 introns. This is consistent with the view that not only has there been streamlining of genomes (through intron loss in invertebrate lineages, evidence mounting from comparison of orthologous gene sets) but there has been a lower incidence of intron gain through such duplication events, compared to mammalian and plant lineages. The fungal genomes that typically have relatively few short introns also are believed to have undergone sweeps of intron removal via reverse transcriptase retrocopies (supported by the bias of introns near 5' ends of genes).

For protists, genomic sequencing data is as yet still at an early stage and most examined have fewer introns than mammals. The introns in *Dictyostelium discoideum* have the shorthand, in the intron-rich *Toxoplasma gondii*, interestingly about 5.3% of the introns have LIN≧5 bp, thus rather similar to plants and vertebrates.

Figure 15:
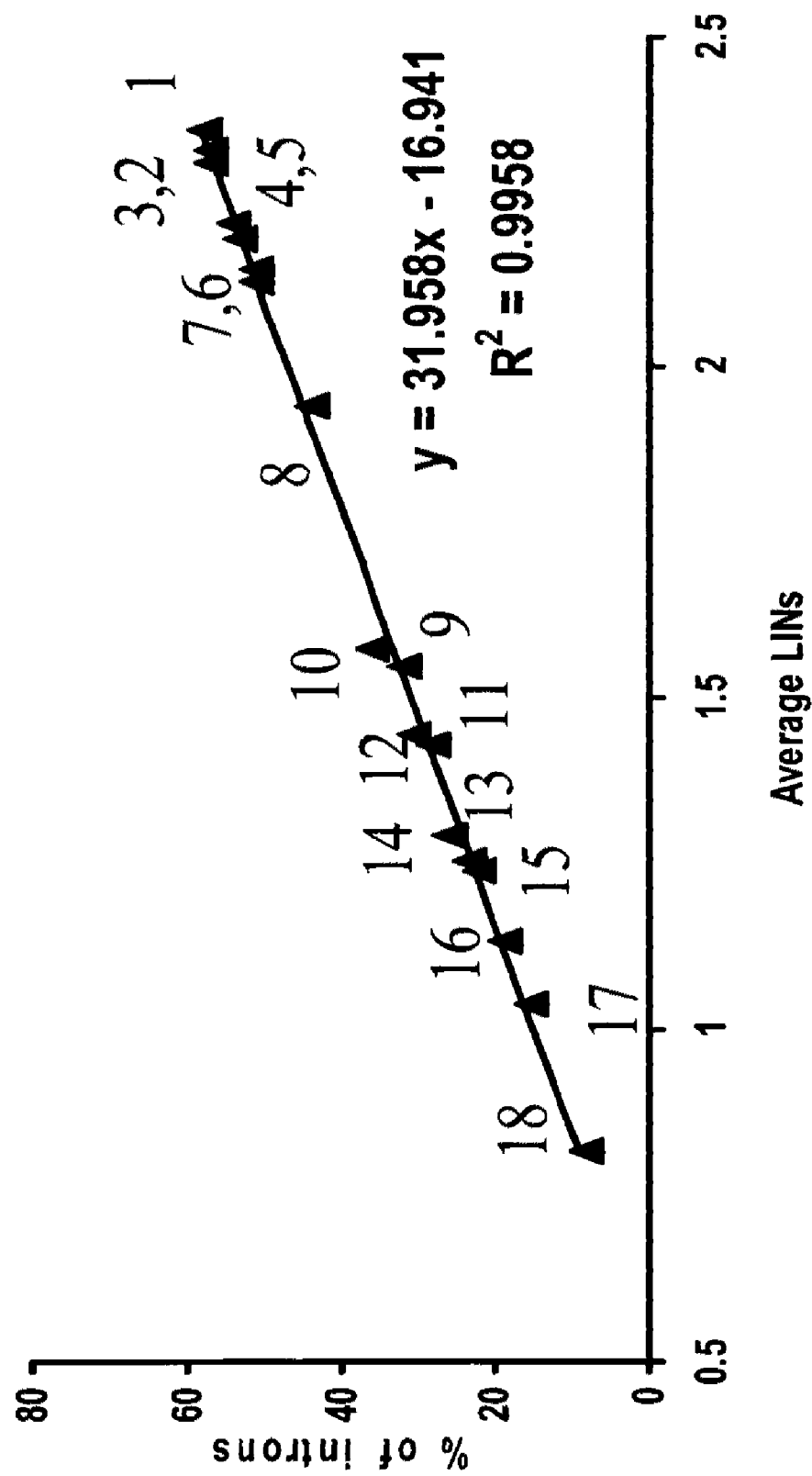
FIG. 15 shows the relationship between LINs and organisms' complexities.
Figure 16:
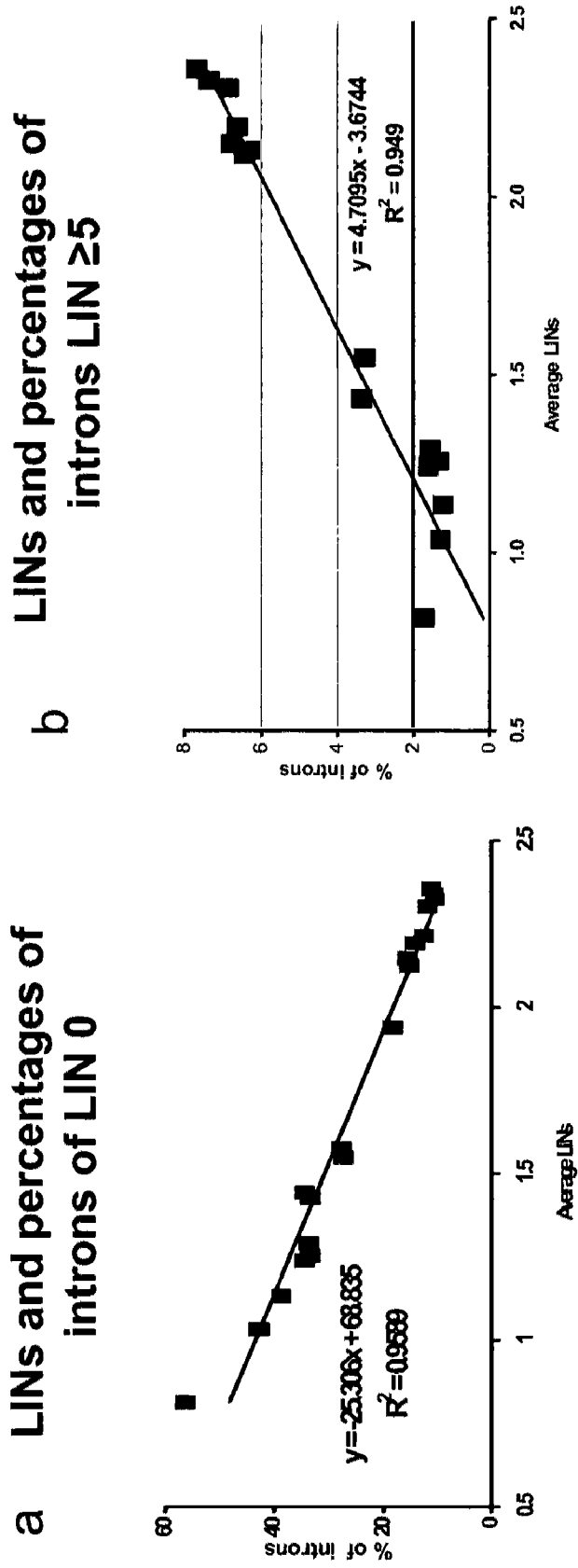
FIG. 16 shows the relationships between LINs and percentage of introns with 0 bp LIN (a) and with the percentage of $\geq 5$ bp LIN introns (b).

As shown in FIGS. 15 and 16, a strong positive correlation has been observed between the overall average LIN and percent overrepresentation (based on randomized sequence expectations) (PORSE) ($R^2$=0.9958; t-test, p ≦$2.94e^{-8}$) and percentage of introns of LIN ≧5 (R2=0.949; t-test, p ≦ $2.02e^{-6}$) as well as negative correlation with percentage of introns of zero LIN ($R^2$=0.9589; t-test, p≦$9.11e^{-8}$) (FIG. 16). The data suggests that parameters such as percentages of intron set of LIN ≧5 bp, excessive percentage (vs. random control), percentage of 0 LIN introns and average LIN will be useful tools in assessing recent intron gain in genomic evolution.

Figure 3:
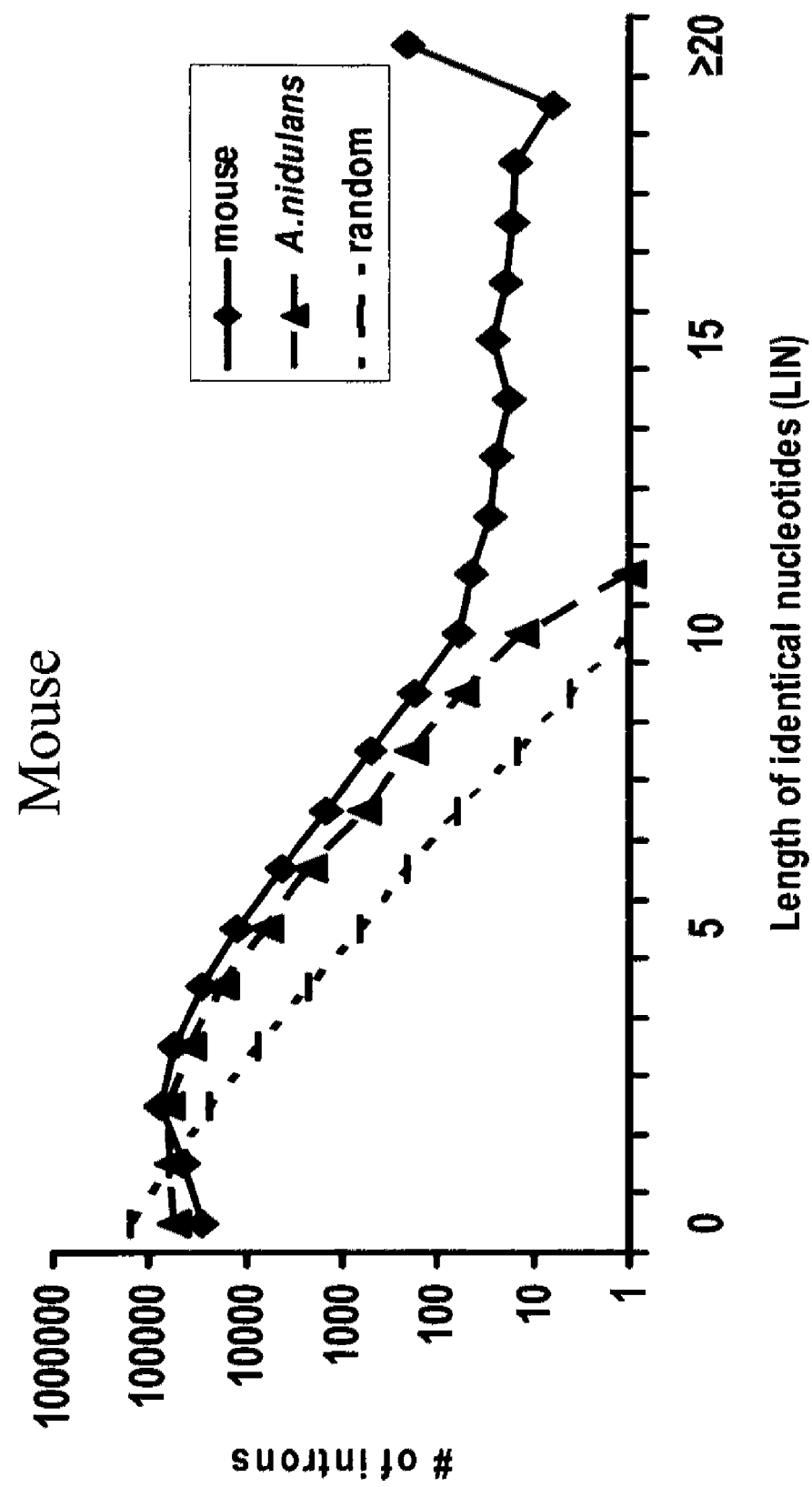
FIG. 3 shows the analysis of the different LIN distribution from the mouse total introns (solid lines). The random sequences (lines) and *Aspergillus nidulans* intron data (triangles) were used as controls.
Figure 4:
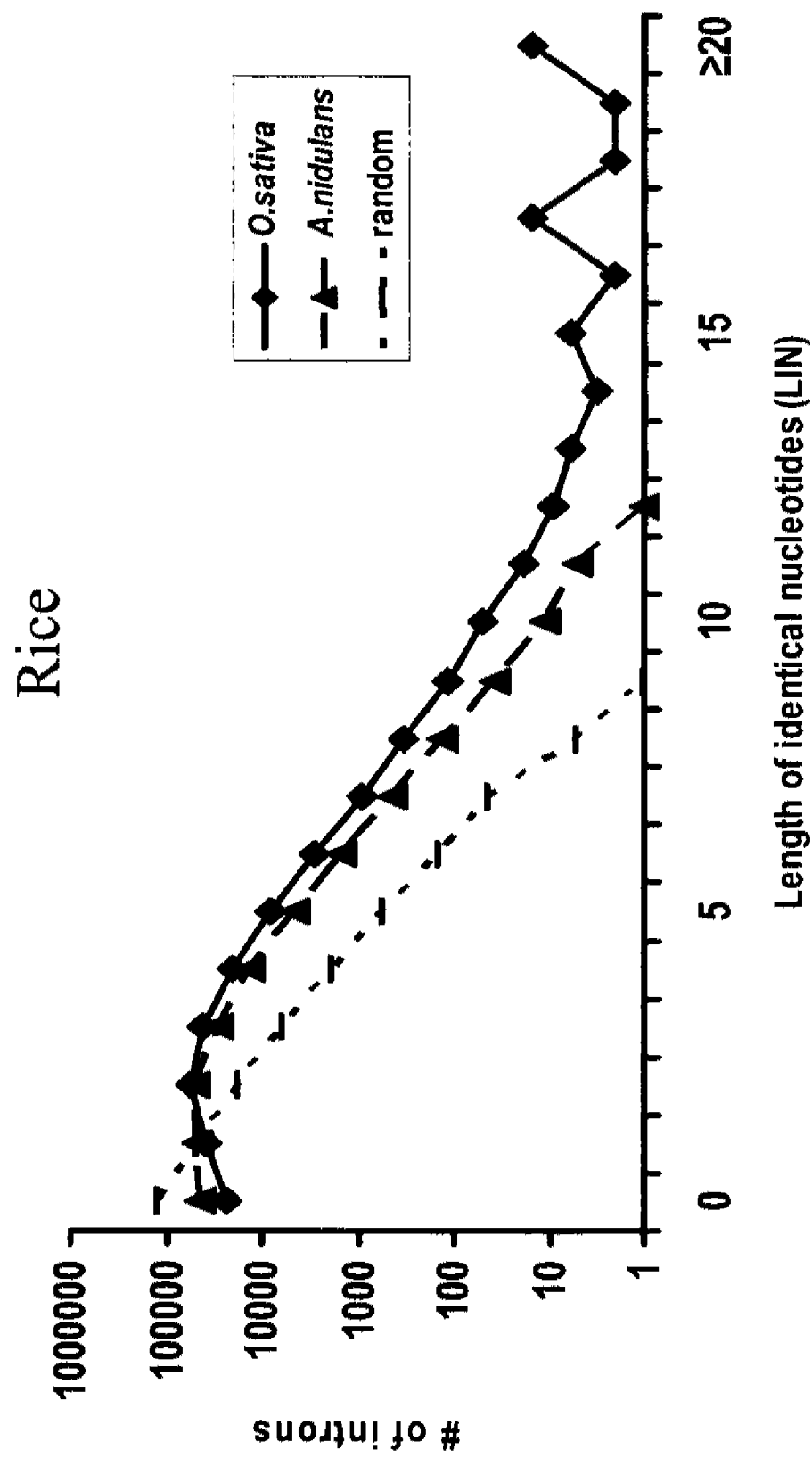
FIG. 4 shows the analysis of the different LIN distribution from the rice total introns (solid lines). The random sequences (lines) and *Aspergillus nidulans* introns (triangles) were used as controls.
Figure 5:
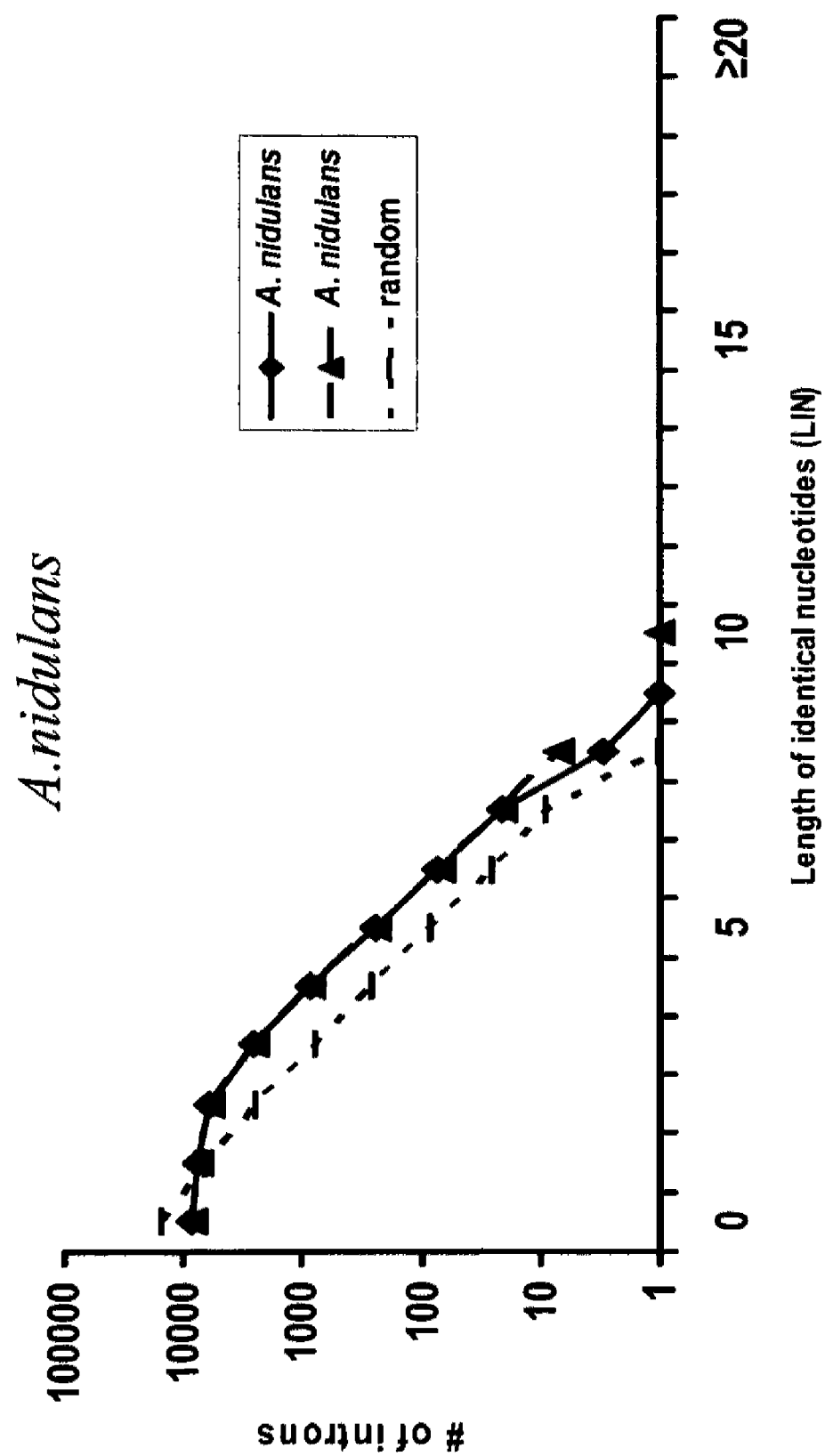
FIG. 5 shows the analysis of the different LIN distribution from the total *Aspergillus nidulans* introns (solid lines). The random sequences (lines) and *Aspergillus nidulans* introns (triangles) were used as controls.
Figure 6:
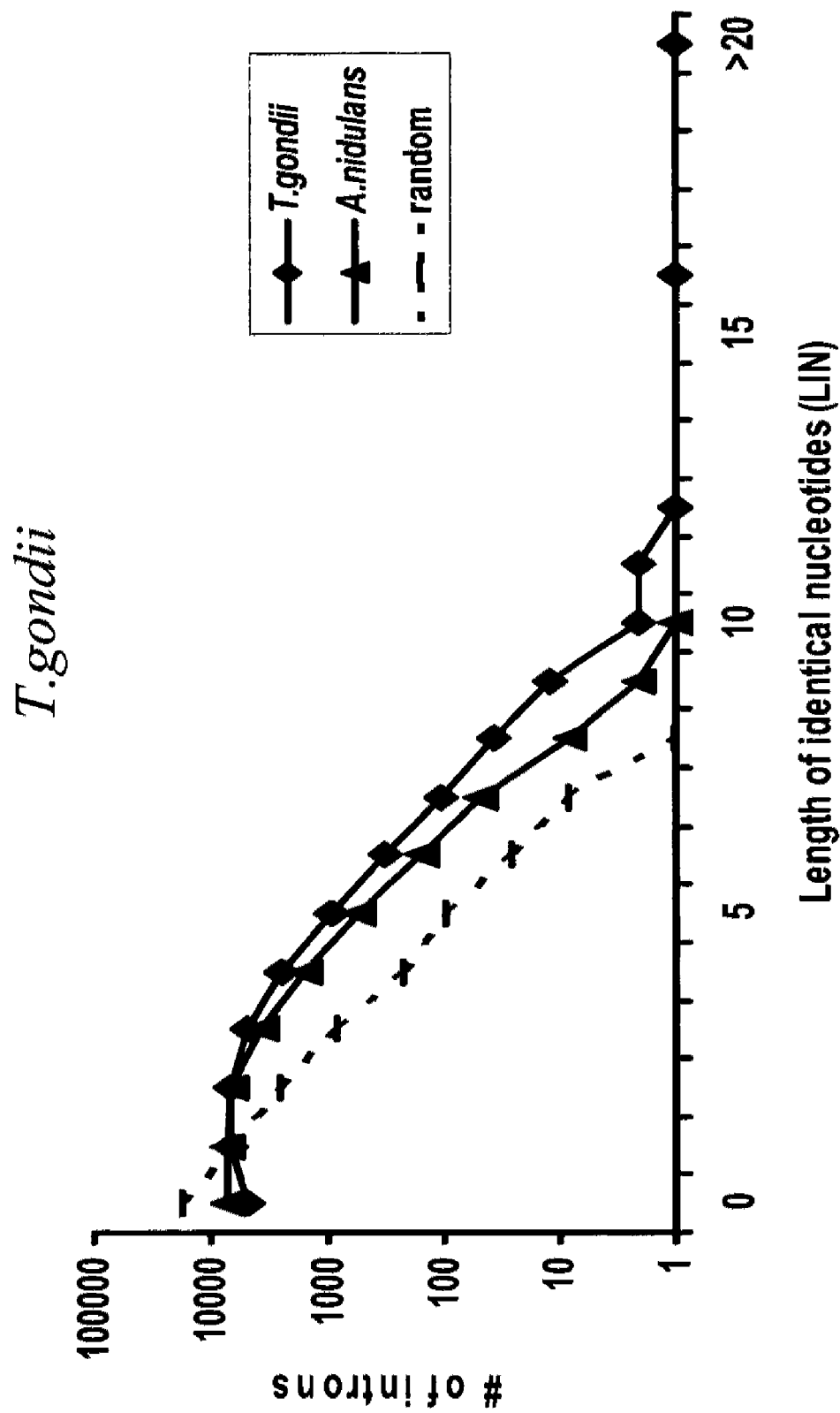
FIG. 6 shows the analysis of the different LIN distribution from the total *T. gondii* introns (solid lines). The random sequences (lines) and *Aspergillus nidulans* introns (triangles) were used as controls.

Many recently-acquired human introns share common ancestors. To determine whether certain nucleotide stretches might be disproportionately represented in long LIN-type introns, and thus might reflect recruitment (or tolerance) of particular sequences in the creation of this type of young introns, the nature of the hexamers immediately upstream and downstream of the 5' splice sites and 3' splice sites were compared. The profiles for these four categories (scored for representation of all possible hexamers) are shown in FIG. 3 for mouse and rice for the total set of introns and the subset of LIN≧10 bp. Relatively long LINs were also chosen to minimize any swamping out effect by known splicing junction consensus motifs (GT-AG).

Figure 17:
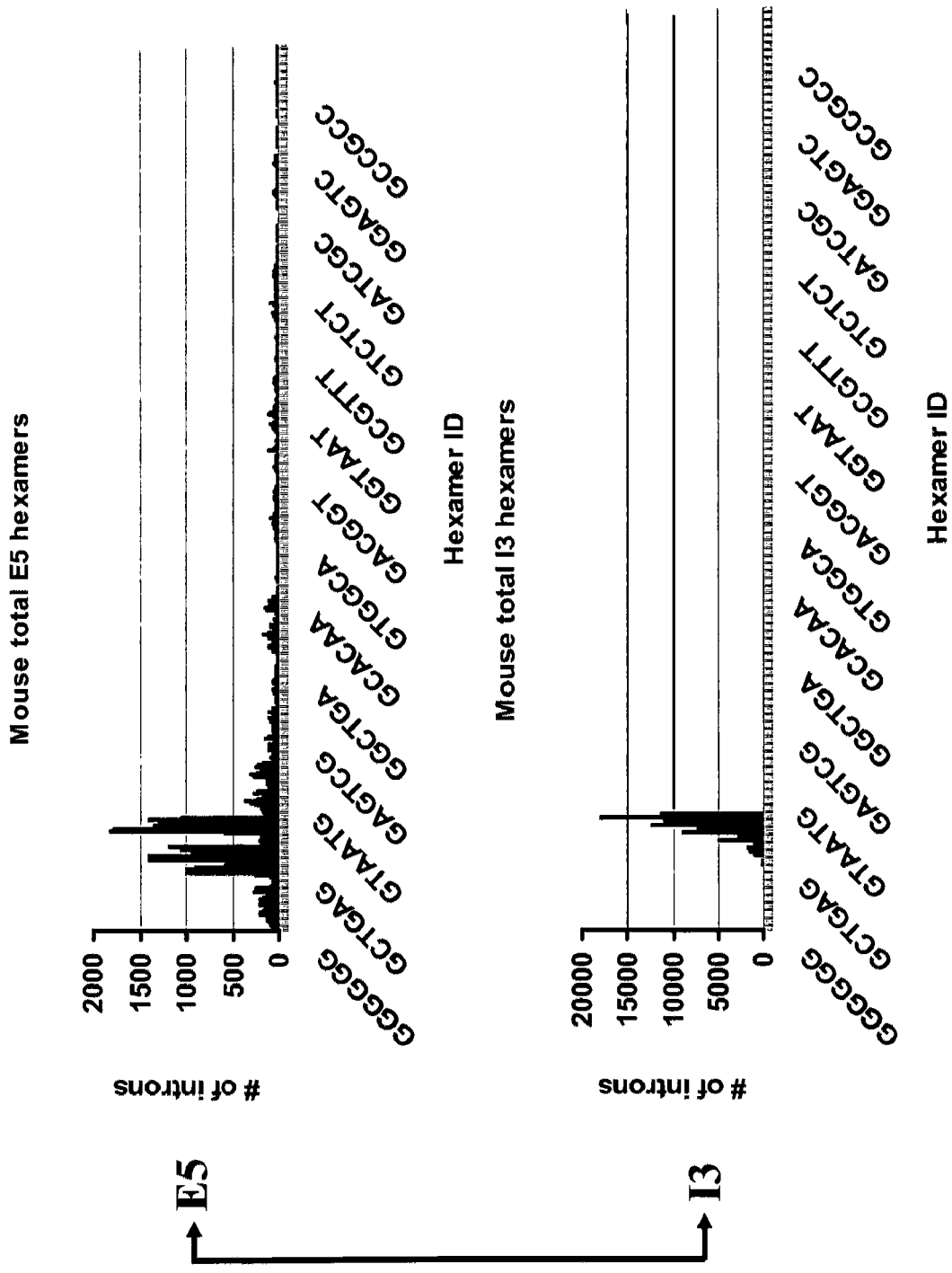
FIG. 17 shows a comparative analyses of the E5 and I3 hexamers from the mouse total dataset.
Figure 18:
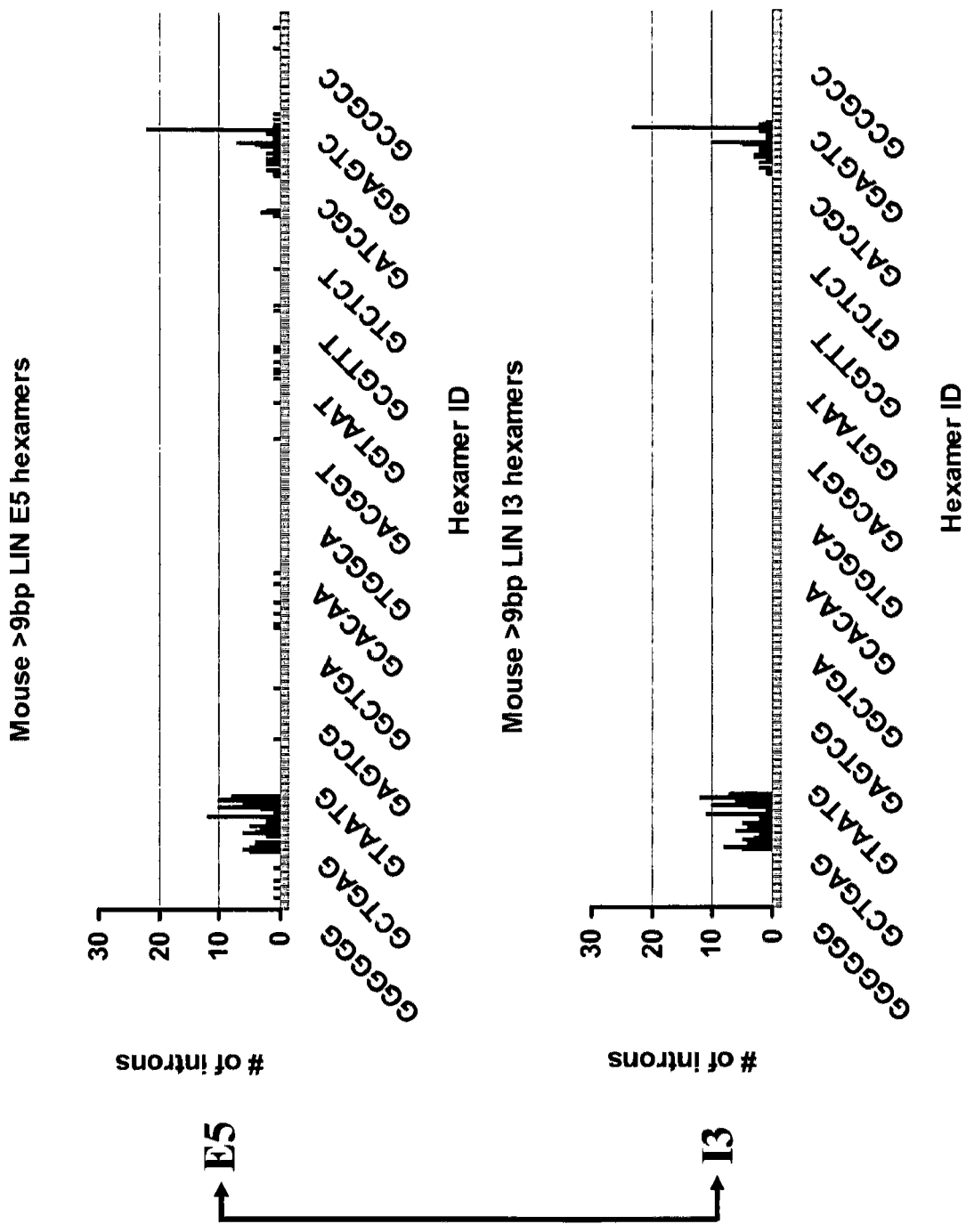
FIG. 18 shows a comparative analyses of the mouse E5 and I3 hexamers from the mouse introns with 10 bp LIN.
Figure 19:
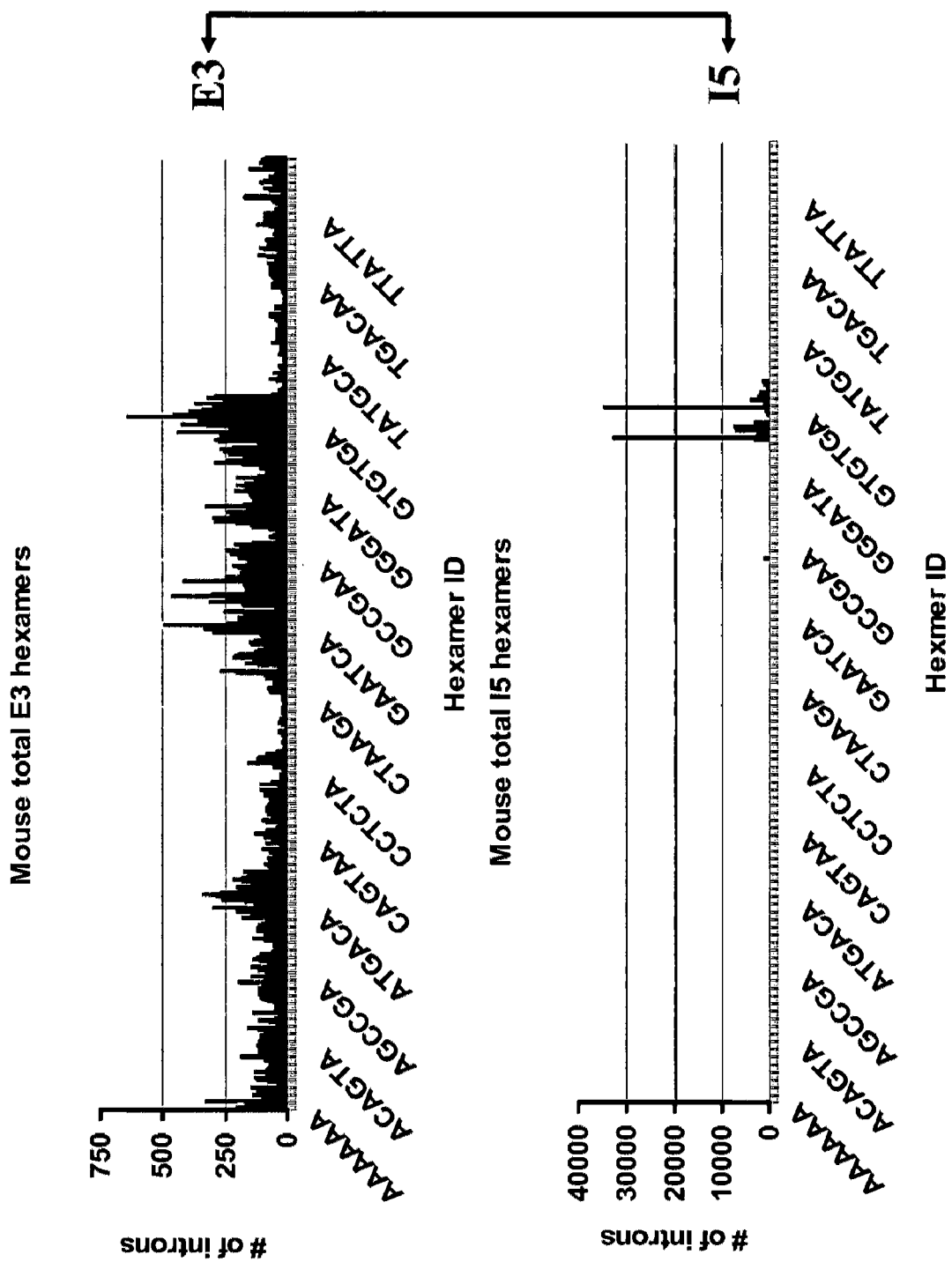
FIG. 19 shows a comparative analyses of the E3 and I5 hexamers from the mouse total dataset.

For the total intron sets, mouse and rice display rather similar profiles (FIGS. 17, 19, 21 and 23), with a much broader spectrum for exon than intron sequences as expected, and there is also more constraint on upstream exon (E5) than on downstream exon (E3) (FIGS. 17 and 19). This appears rather reminiscent of group II introns, and constraints imposed by base-pairing between IBS-EBS stretches. As expected I5 is highly constrained by pressure imposed by complementarities to U1 snRNA and this is reflected by two striking peaks in mouse and a tight cluster in rice (the two highest of which are the same sequences as the mouse ones, GTPuAGT). At the 3' end of the intron (I3), again there is representation of only a few of all possible hexamers.

Figure 20:
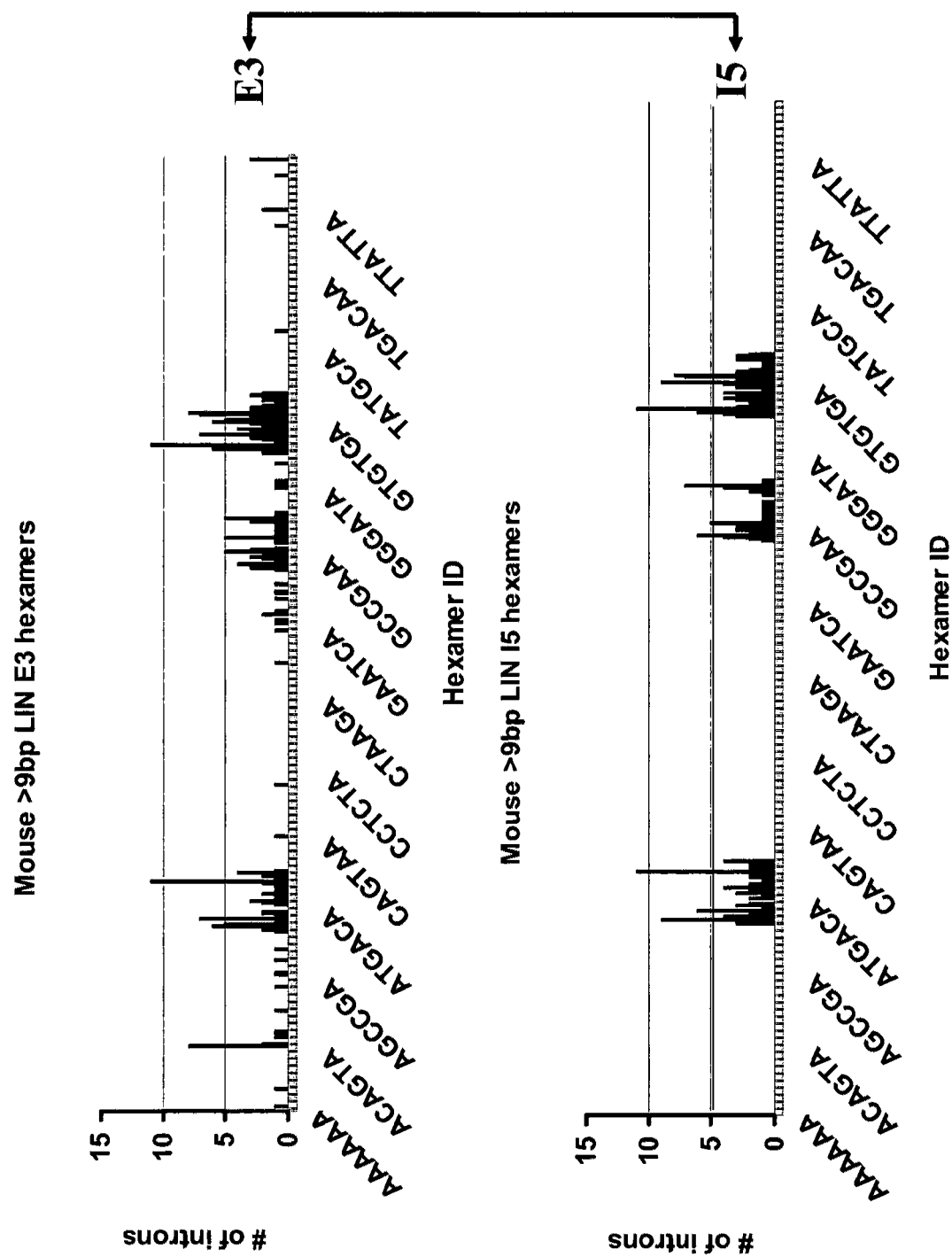
FIG. 20 shows a comparative analyses of the mouse E3 and I5 hexamers from the mouse introns with $\geq 10$ bp LIN.
Figure 21:
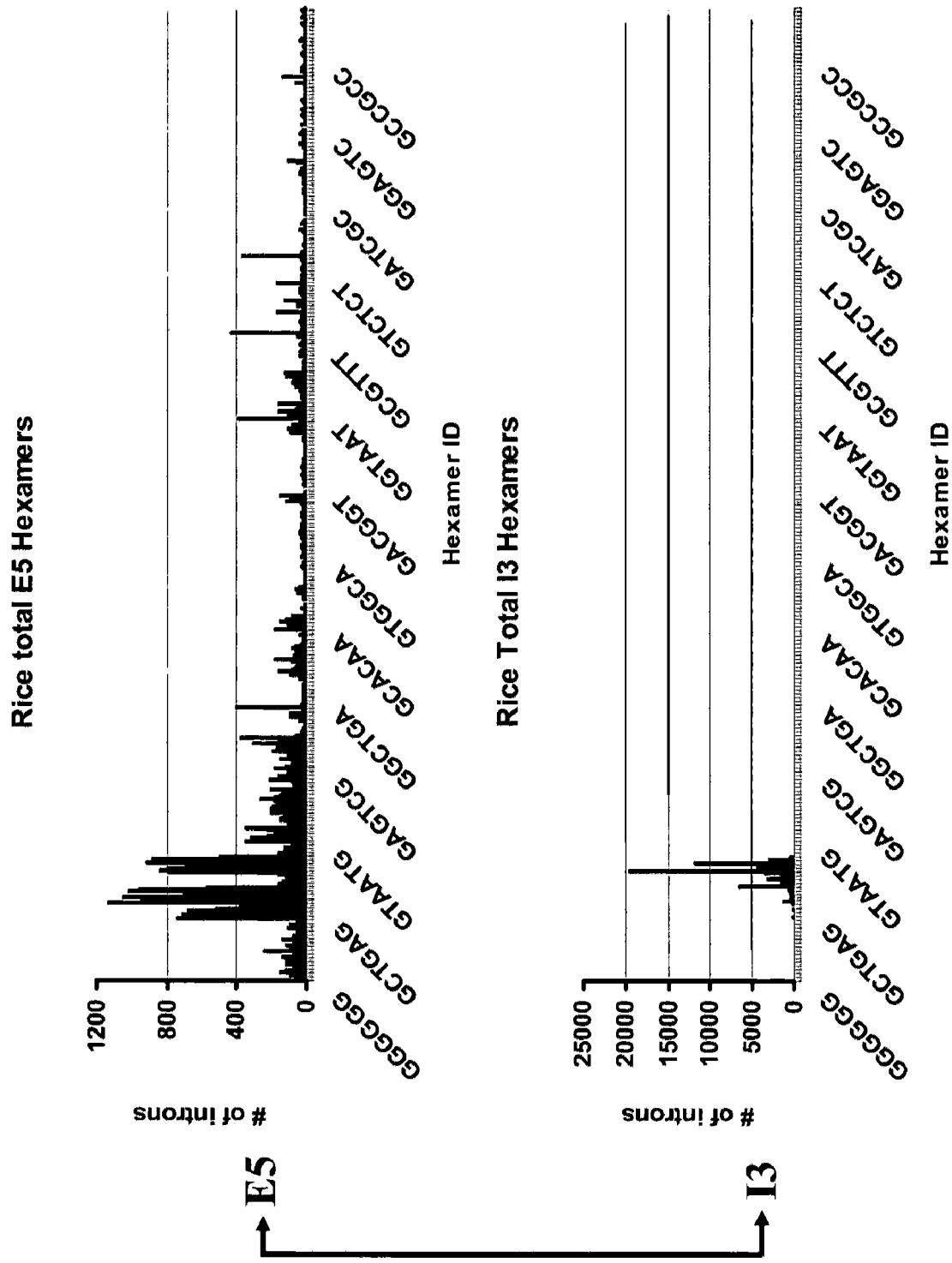
FIG. 21 shows a comparative analyses of the E5 and I3 hexamers from the rice total dataset.
Figure 22:
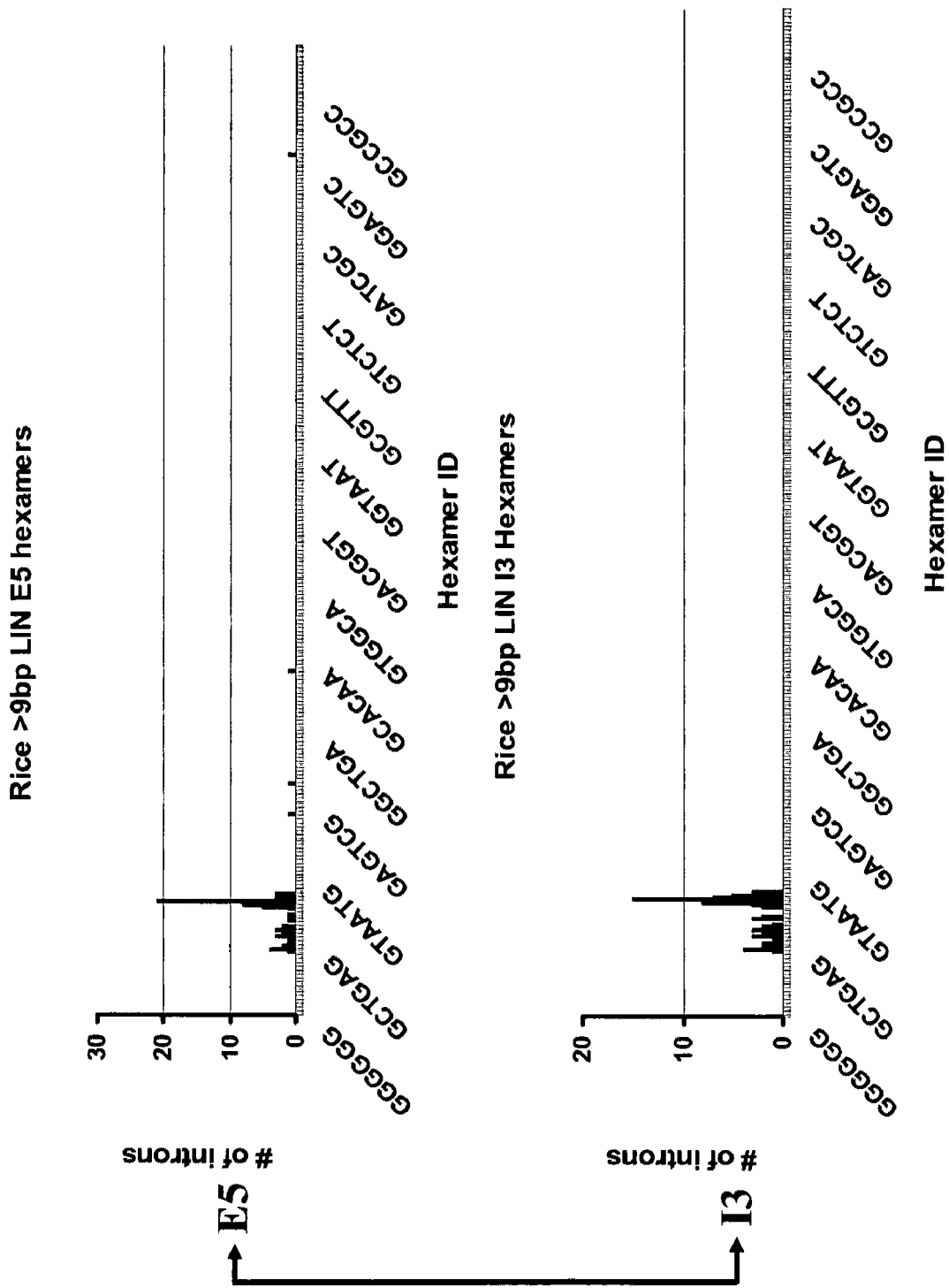
FIG. 22 shows a comparative analyses of the mouse E5 and I3 hexamers from the rice introns with $\geq 10$ bp LIN.
Figure 23:
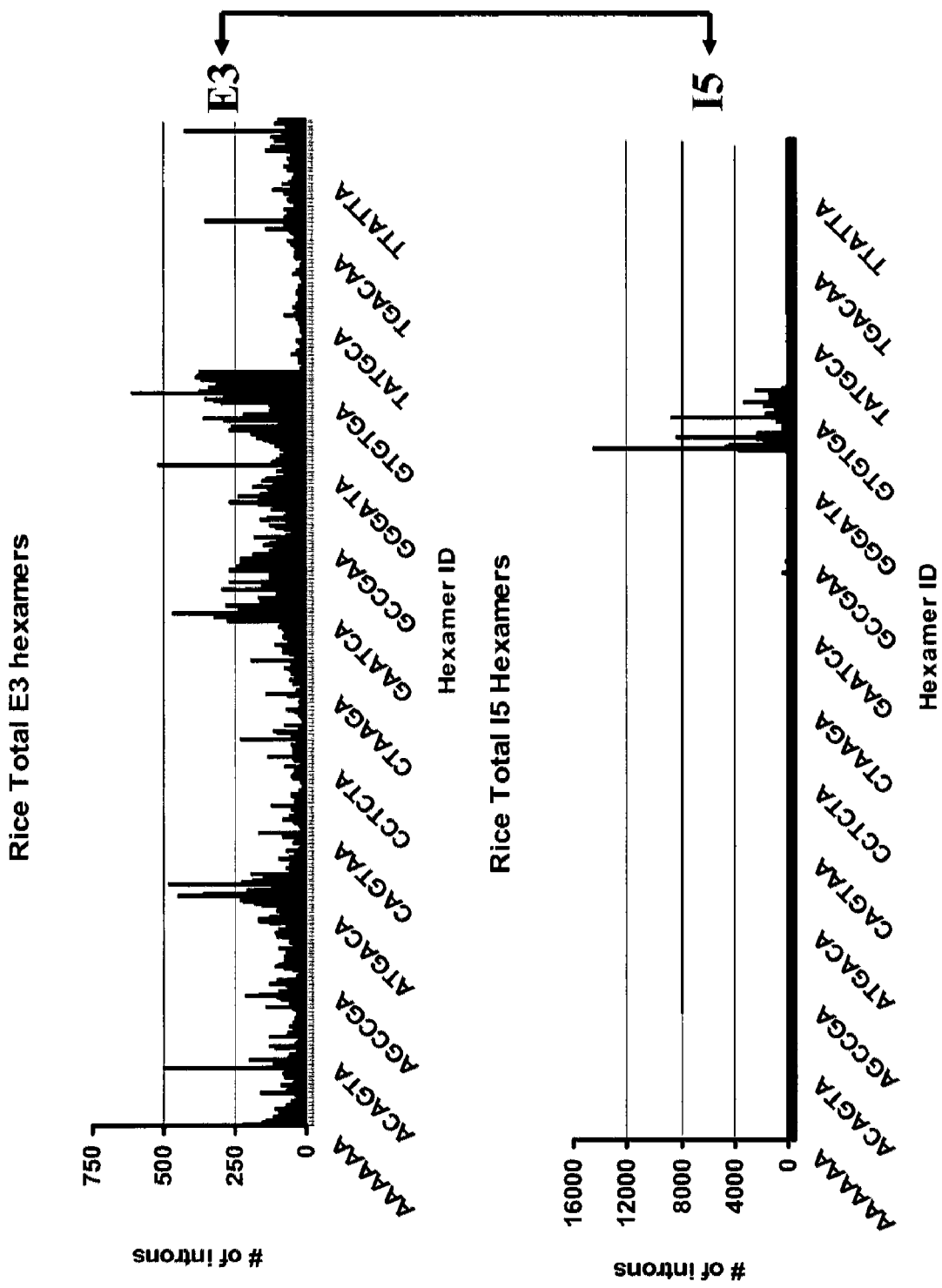
FIG. 23 shows a comparative analyses of the E3 and I5 hexamers from the rice total dataset.

The profiles for the subset of LIN ≧10 intron class for mouse and rice are strikingly different from the total intron set (FIGS. 18, 20, 22 and 24) and also show some differences between plants and animals. The similarity of E5 and I3 profiles highlights their repeated nature, as do the I5 and E3 profiles. The hexamer peaks of introns LIN ≧10 for mouse and rice differ in sequence (and the same holds for human and *Arabidopsis*, FIG. 25), consistent with different sequences having contributed to recent intron gains independently in the different lineages. The three clusters seen for mouse I5 (and less prominently for E3) represent the canonical GT-AG, and minor GC-AG and AT-AC intron categories peaks (in that order in FIG. 20) reflecting a disproportionately high representation of the latter two compared to the total intron set. This is consistent with the idea that splice sequence has not yet been "polished" by evolution to the consensus sequence and indeed many fall in the category of alternative splicing type (perhaps in the process of trial-and-error prior to fixation). In contrast, rice has primarily the GT-AG type. Although it is difficult to track the origin of the specific highly-abundant sequences, the peak hexamer from mouse introns of LIN ≧10 (which comprises 5% of that class) is a low complexity sequence, ACACAC. The most abundant rice E5 hexamer is TCACAG, which might reflect part of a putative mutate-like transposase sequence.

Figure 24:
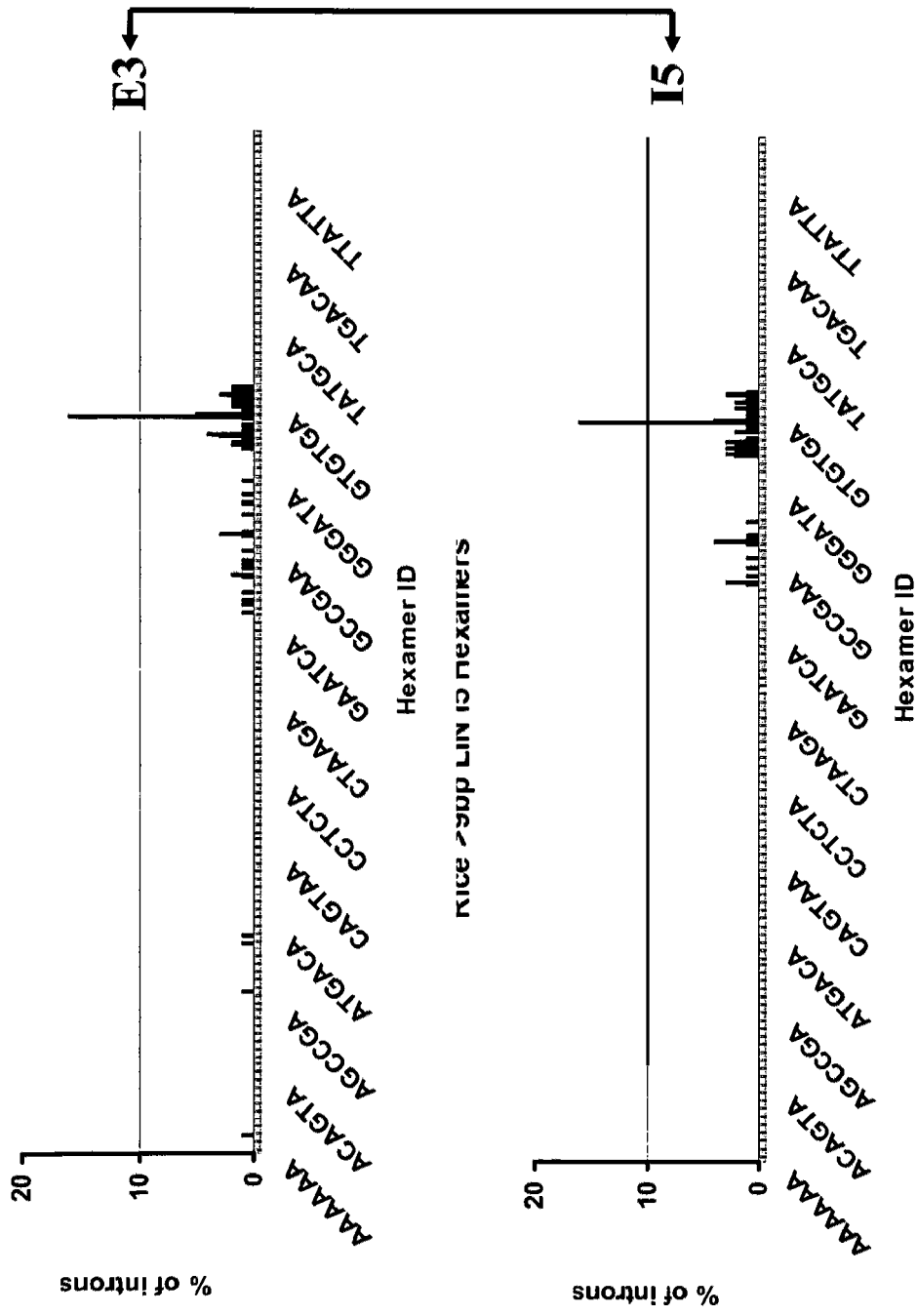
FIG. 24 shows a comparative analyses of the mouse E3 and I5 hexamers from the mouse introns with $\geq 10$ bp LIN.
Figure 25:
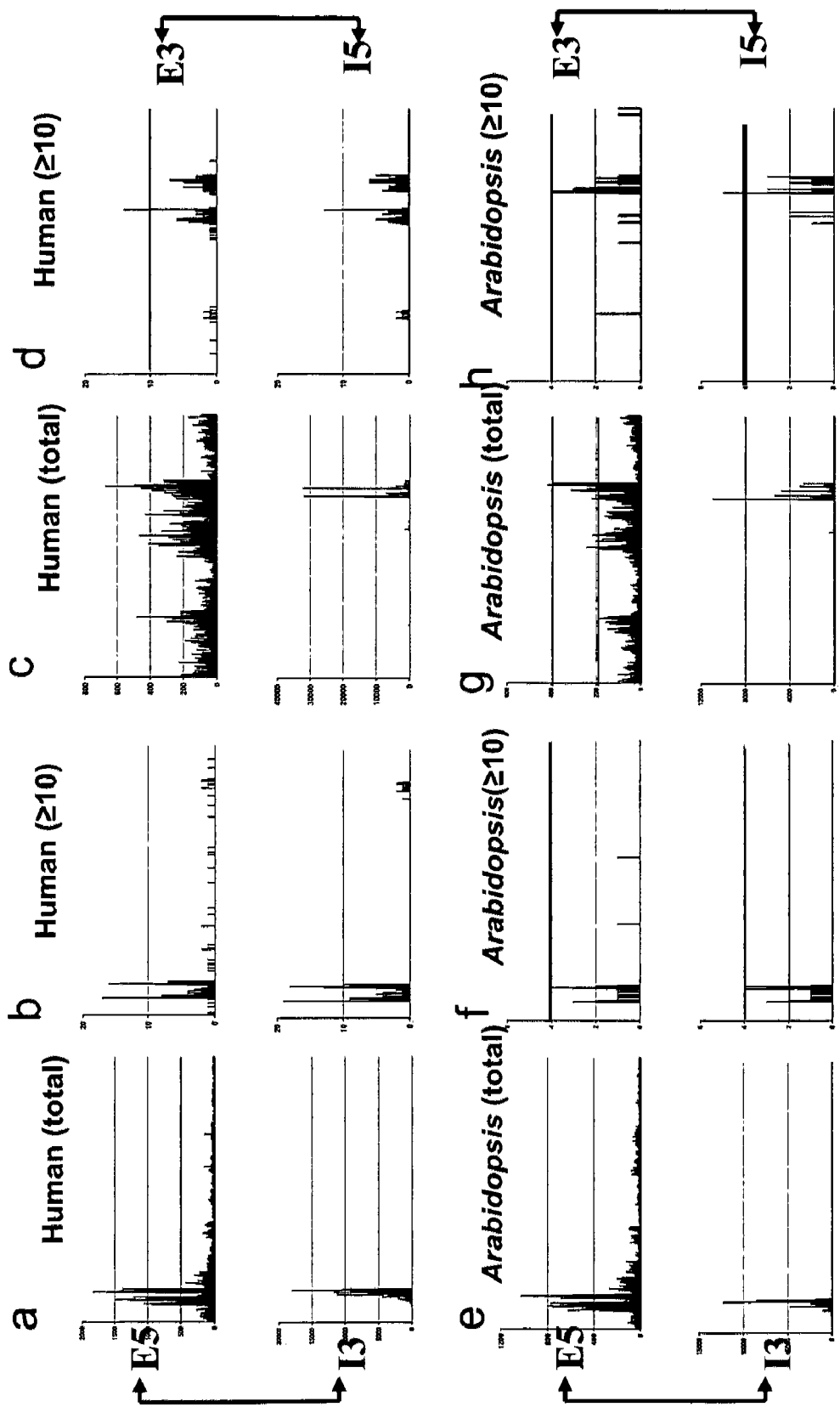
FIG. 25 shows a comparative hexamer analysis of the total introns and introns of $\geq 10$ bp LIN between human and *Arabidopsis*.

It is expected that as time passes after intron creation through a segmental duplication process that the LIN value will become smaller. To test this notion, we selected a group of 16 introns located at the identical position within nuclear-located mitochondrial ribosomal protein genes in human and *Arabidopsis*. This is consistent with "early transferred genes" and a long history in these nuclear genes, that is prior to the human/plant split. This set was compared with ones for ribosomal protein genes which are still present in the mitochondria in protist and/or plant lineages, but are in the nucleus in the animal lineage. The "early" and "late" introns have average LIN of 1.62 bp and 2.67 bp, respectively (t-test, p<0.05) and the "early" intron LIN is 60% smaller than the "late" one. To confirm the "early" introns have, on average, shorter LIN than the "late" introns, we aligned the conserved proteins from different lineages of eukaryotic organisms. As shown in FIG. 24, the introns whose positions are shared by all different lineages of eukaryotes (indicated by arrows) have much shorter LINs than Glade-specific introns (marked by asterisks). Many Glade-specific introns are located close to 5' and 3' portions of the genes.

Figure 26:
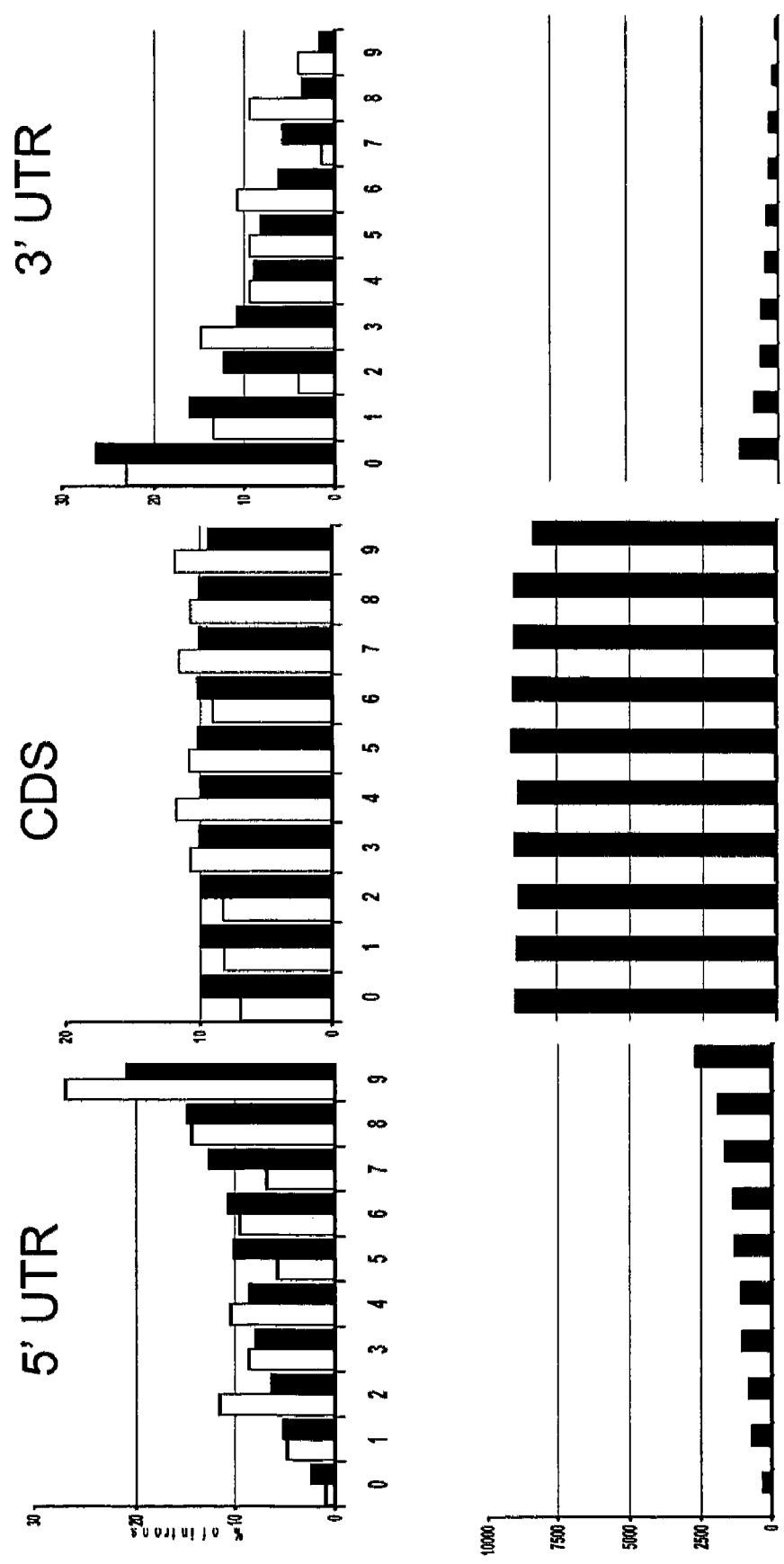
FIG. 26 shows introns positions in 5' UTR, CDS and 3' UTR from the mouse intron dataset. The relative positions are classified into categories of 0 to 9. Each category is determined by an intron location in a region divided by the total number of nucleotides of this region and multiplied by 10. Top and lower panels represent Relative proportions of total mouse introns and introns of LIN $\geq 10$ in 5' UTR, CDS and 3" UTR and absolute numbers of introns.
Figure 27:
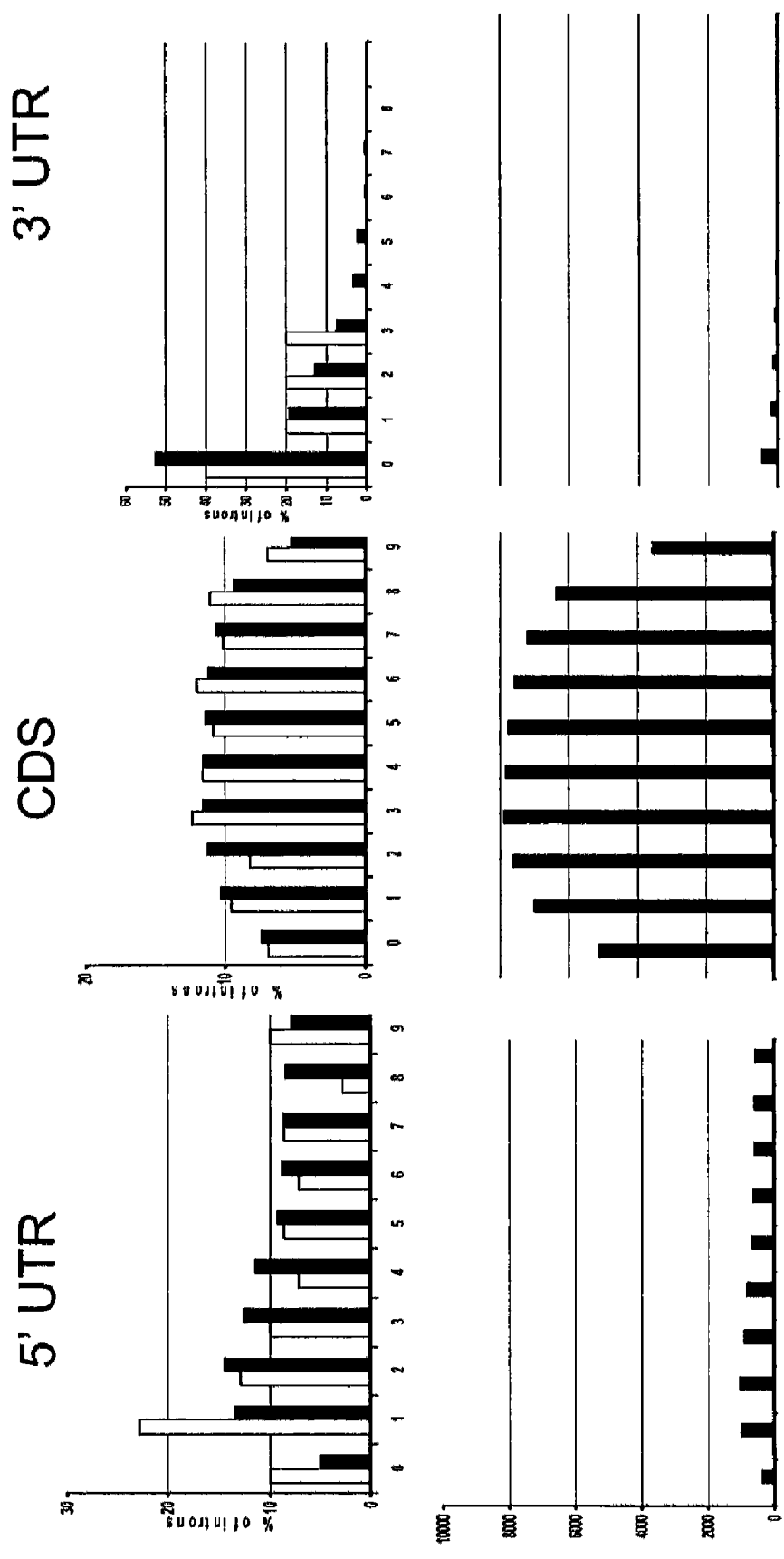
FIG. 27 shows introns positions in 5' UTR, CDS and 3' UTR from the rice intron dataset. The relative positions are classified into categories of 0 to 9. Each category is determined by an intron location in a region divided by the total number of nucleotides of this region and multiplied by 10. Top and lower panels represent Relative proportions of total mouse introns and introns of LIN $\geq 10$ in 5' UTR, CDS and 3" UTR and absolute numbers of introns.
Figure 28:
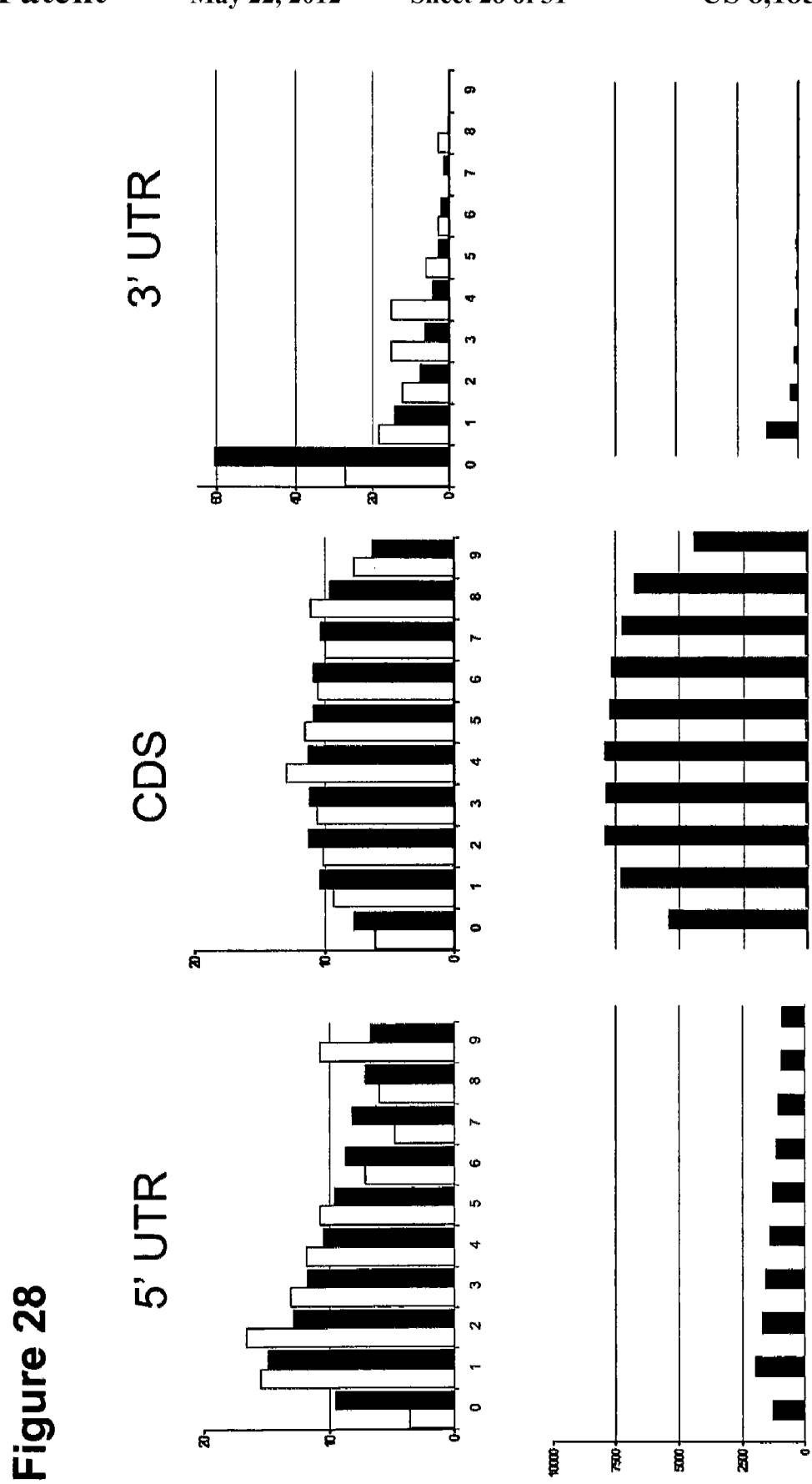
FIG. 28 shows introns positions in 5' UTR, CDS and 3' UTR from the human intron dataset. The relative positions are classified into categories of 0 to 9. Each category is determined by an intron location in a region divided by the total number of nucleotides of this region and multiplied by 10. Top and lower panels represent Relative proportions of total mouse introns and introns of LIN $\geq 10$ in 5' UTR, CDS and 3" UTR and absolute numbers of introns.
Figure 29:
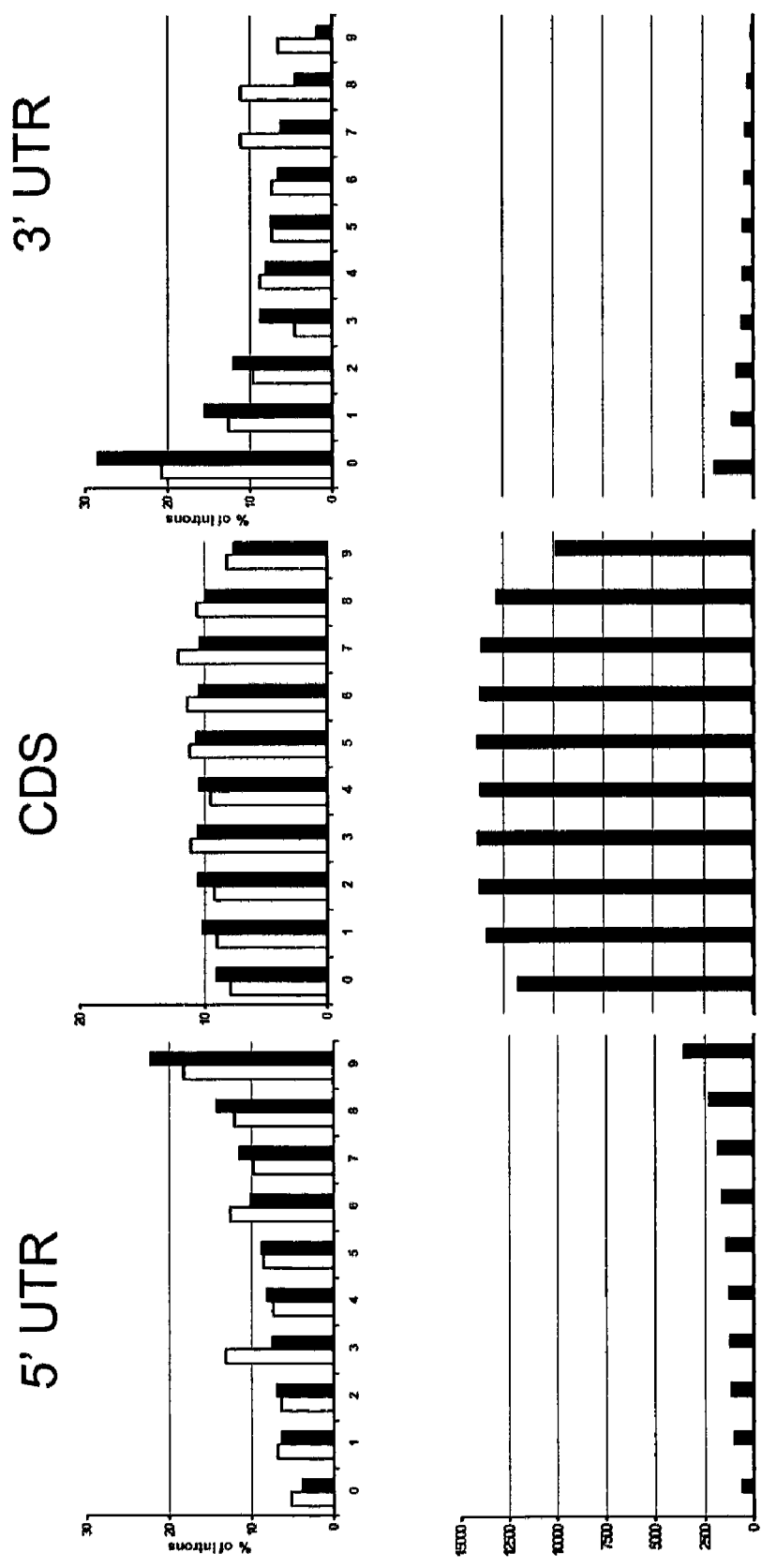
FIG. 29 shows introns positions in 5' UTR, CDS and 3' UTR from the *Arabidopsis* intron dataset. The relative positions are classified into categories of 0 to 9. Each category is determined by an intron location in a region divided by the total number of nucleotides of this region and multiplied by 10. Top and lower panels represent Relative proportions of total mouse introns and introns of LIN $\geq 10$ in 5' UTR, CDS and 3" UTR and absolute numbers of introns.
Figure 30:
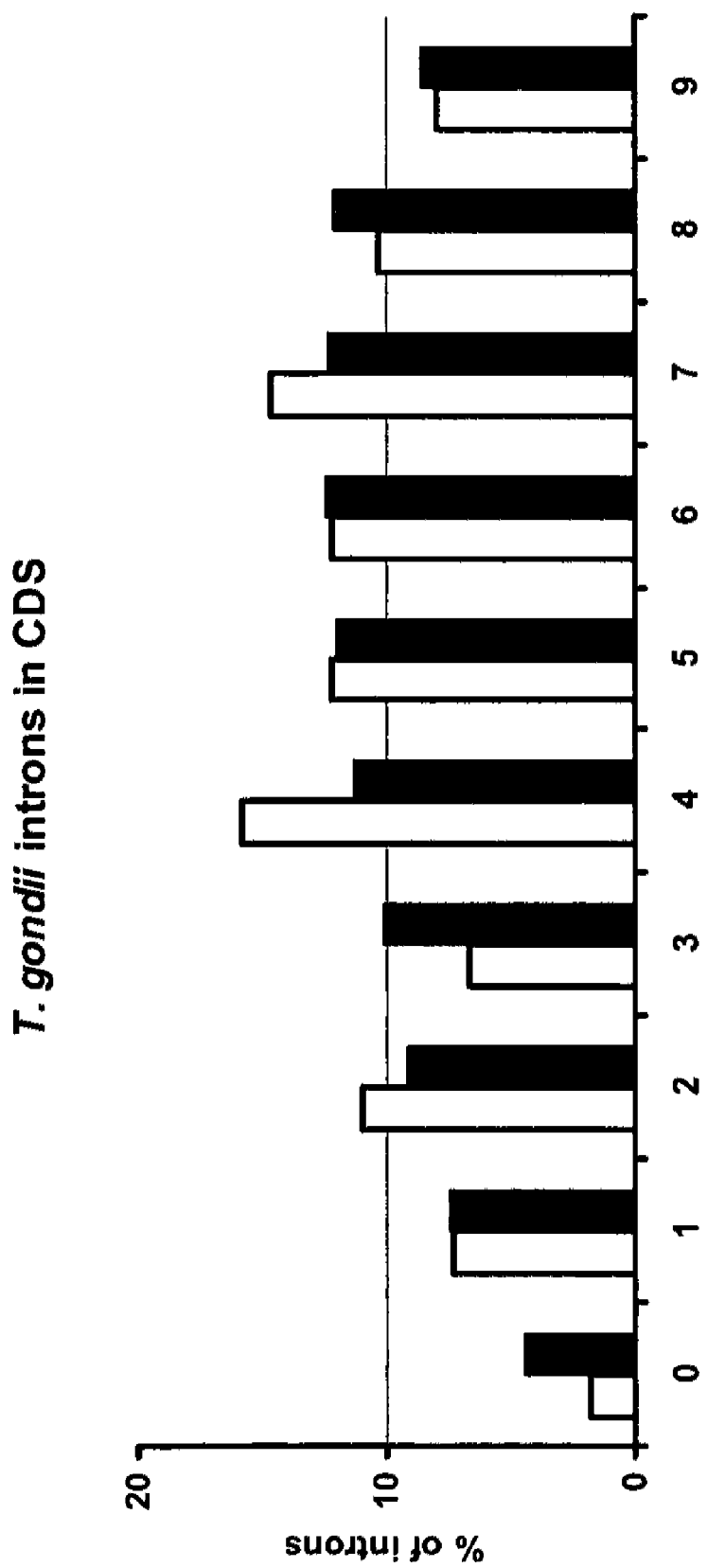
FIG. 30 shows introns CDS positions of *T. gondii*. The CDS region is divided into categories of 0 to 9. Each category is determined by an intron position in the CDS divided by the total number of nucleotides of this region and multiplied by 10.
Figure 31:
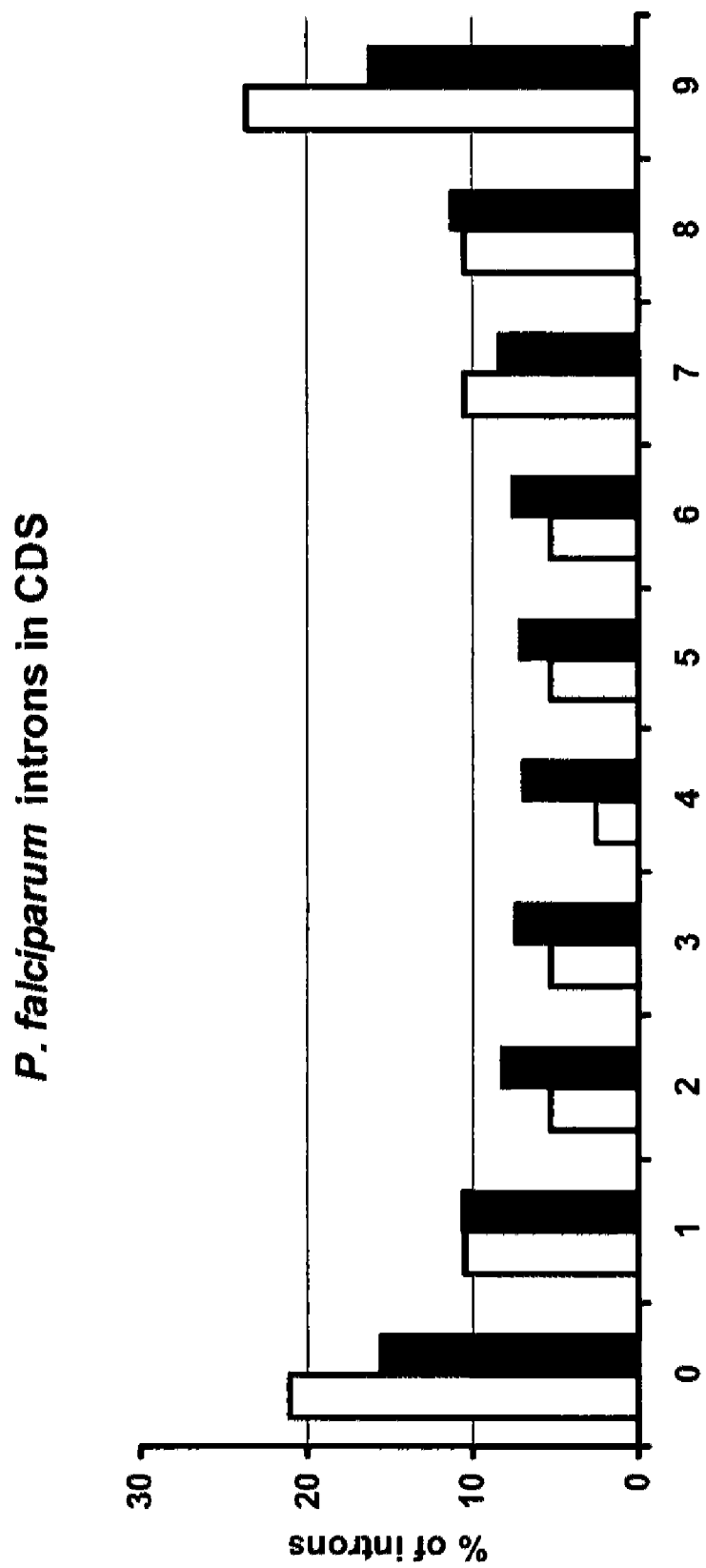
FIG. 31 shows introns CDS positions of *P. falciparum*. The CDS region is divided into categories of 0 to 9. Each category is determined by an intron location in the CDS divided by the total number of nucleotides of this region and multiplied by 10.

There is some supporting evidence that intron gain tends to preferentially occur at the ends of genes (5' UTR or 3'UTR region), that is that genes may "grow in length" over evolutionary time (perhaps mediated by alternative splicing during the initial stages). For example, it has been suggested that in human and *Arabidopsis* that the gain of introns in the 3' portion of genes is a dominant process. In contrast, old introns tend to show a bias for position in the 5' regions of genes consistent with sporadic loss of ones located toward the 3' end via an RT-mediated process. Such a trial-and-error process would be expected to be more easily tolerated in UTRs than within coding sequences. We observed that approximately 80% of introns are within coding sequences for rice and mouse, 15% in 5'UTRs and 5% in 3'UTR. The distributions of the intron of LIN ≧10 are similar to those of the total datasets for both rice and mouse. The most mouse 5'URT introns were close to coding-regions while those from rice are located further upstream (FIG. 26). Intron from higher plants and vertebrates are generally uniformly distribution in contrast to those from protists and fungi FIGS. 26-31). These data suggest that importance of introns' locations were greatly reduced by alternative splicing.

Our observations reveal new distinctive features of young introns in diverse eukaryotic lineages. In complex multicellular organisms such as plants and vertebrates, there much higher number of recently-acquired introns (compared to fungi and certain protists) correlates with alternative splicing (and plasticity of 5' splice sites) in multicellular organisms. Interestingly, the intron-rich protist, Toxoplasma, also appears to have many young introns arising from segmental duplication suggesting a commonality in mechanism in intron gain.

Experimental Methods
Intron Datasets

The AceView annotated human gene data (AceView NCBI Build35) were downloaded from the website of ncbi.nlm.nih.gov/IEB/Research/Acembly, the mouse NIA gene index (Version 5) from the website of lgsun.grc.nia.nih.gov/geneindex5/, the *Caenorhabditis elegans* gene annotation and sequence data (WS170) from the ftp website of wormbase-.org/pub/wormbase/ and the *Drosophila melanogaster* annotation and sequence from the website of flybase.net/annot/. The exon-intron dataset from zebrafish (*Danio rerio*) (release Zv4) was downloaded from the Exon-Intron Database (hsc.utoledo.edu/bioinfo/eid/). Rice (Release 5) and *Arabidopsis* genome annotations were downloaded from the website of tigr.org/tdb/e2k1/osa1/and the ftp website of tigr.org/pub/data/a_thaliana/, respectively. *Aspergillus nidulans* genome annotation dataset and sequences was downloaded from the website of broad. mit.edu/annotation/genome/aspergillus_group/MultiHome.html. Sequence and annotations of *Dictyostelium discoideum* were downloaded from the website of dictybase.org/Downloads/. *Toxoplasma gondii* genome annotation and sequence data (4.2) were downloaded from the website of toxodb.org/common/downloads/. All other sequence data were downloaded from the website of hgdownload.cse.ucsc.edu/downloads.html.

Prior to analysis, steps were taken to remove misalignments, computation errors and dubious cDNA and genomic alignments. The human intron dataset from AceView (NCBI Build35) was selected from the transcripts supported by at least one cDNA and/or more than four ESTs with >99% identities to the genomic sequences. The mouse intron data were selected from the NIA-5 U-clusters with support of cDNA and/or at least five ESTs. The intron data from zebrafish were parsed from the Exon-Intron Databases, which have significant proportions of gene annotations by computational prediction. The rice, *Arabidopsis, C. elegans* and *D. melanogaster, A. nidulans* intron datasets were selected from the gene annotations with support of cDNAs and ESTs. Only GT-AG, GC-AG and AT-AC types of introns were included in the datasets.

Splice Junction Analysis

Figure 2:
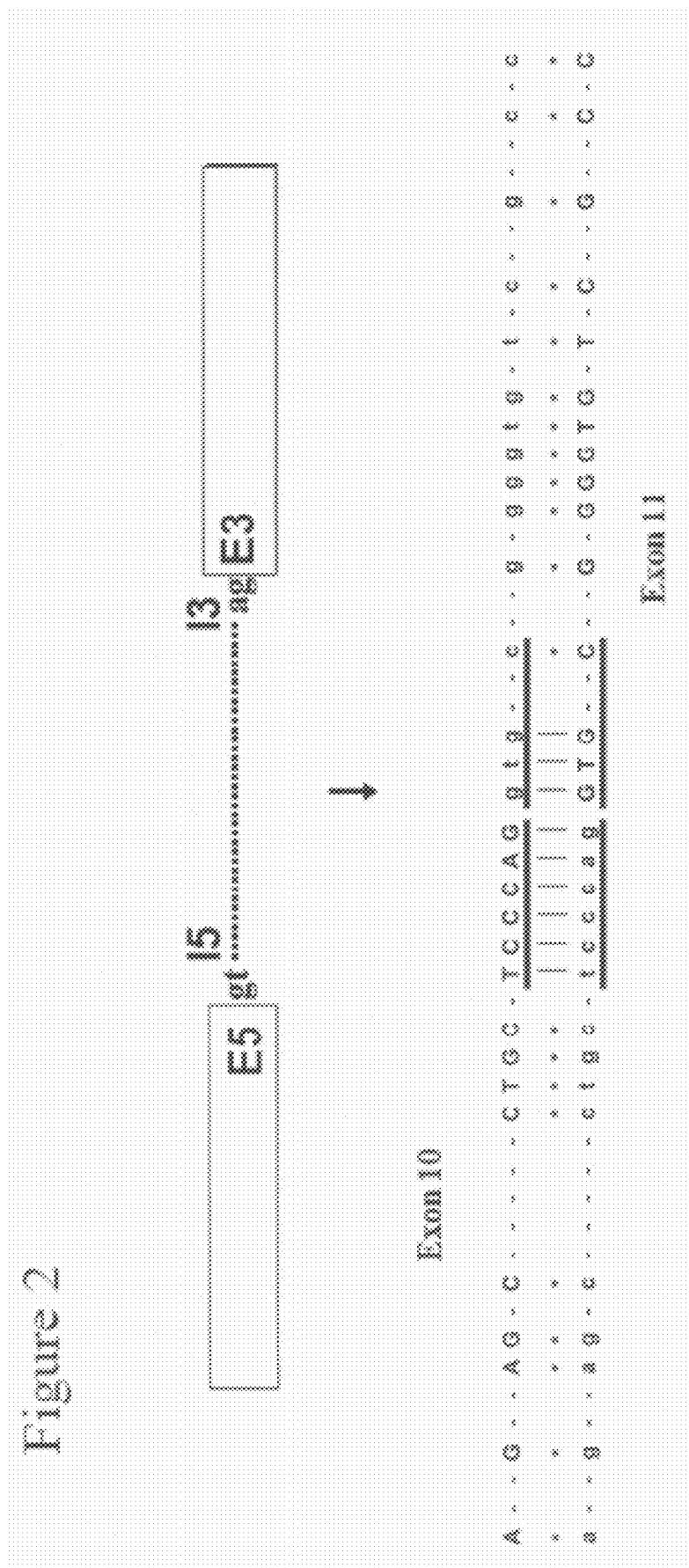
FIG. 2 schematically represents alignments between 5' splice junction (designated as E5 and I5) and the 3' splice junction (designated as I3 and E3) for 1,827 bp intron 10 of mouse Tbc1d2 gene encoding TBC1 domain family, member 2 (NM_198664) used in this research. The upper left and right rectangular sections schematically represent 5' and 3' exonic sequences, respectively. The dashed line schematically represents the intron sequence. Nucleic acid sequences lacking homology are identified as "–".

5' splice sites were divided into 5' exonic (E5) and 5' intronic (I5) splicing sequences and 3' splice sites into 3' intronic (I3) and 3' exonic (E3) splicing sequences, as shown in FIG. 2. The E5 sequence (uppercase black) was aligned with I3 sequence (lowercase) from positions −1 to −150 and the I5 sequence (italicized lowercase) was aligned with E3 sequence (italicized uppercase) from positions 1 to 150. The number of uninterrupted identical nucleotides was scored outwards from the splice sites, independently for the E5-I3 and I5-E3 alignments. These two scores were summed together as the length of identical nucleotides (LIN). The introns of LIN >20 were classified into category of ≧20.

To check whether observed results might be due to random consequences, the E5 and I3 sequences were scrambled with I3 and E5 sequences randomly selected from the same intron dataset while the I5 and E3 sequences were aligned with the randomly-selected E3 and I5 sequences. To minimize effects by gene duplications and intron duplications and to make comparison possible among different lineages of eukaryotic species, *A. nidulans* intron dataset was used as a control. That is, the E5 and sequences were scrambled with I3 and E5 sequences randomly selected from *A. nidulans* intron dataset and similarly I5 and E3 sequences were mix-and-matched with E3 and I5 sequences. In addition, the comparisons were made with randomized forms of these intron sequences.

Hexamer Distribution Analysis

The six nucleotides immediately upstream and downstream of splice junctions were sorted in the order G, A, T and C with the first nucleotides being weighted least and the last nucleotides weighted most. Subsequently, the I5 and E3 hexamer sets were resorted by Excel in order of A, C, G and T for presentation purposes (so that the most biologically important nucleotides were weighted most, i.e. the first nucleotides of the 5' end of an intron vs. the last nucleotides of the 3' end of an intron).

Intron Distribution

The position of an intron is represented by relative location at one of the regions (5' UTR, CDS, 3' UTR) and classified into one of the categories of 0 and 9. Each category was determined by the location of the intron divided by the total number of nucleotides of the regions and then multiplied by 10.

Statistical Analysis

The means and variances for binomial data were calculated using
$u = Np$ and $\sigma_x^2 = Npq$, where p is the probability that a given event has occurred, q is the probability that the event has not occurred and N is the population of the event. For the continuous data, the equations of $$u = \frac{\sum X_i}{N},$$

$$\sigma^2 = \frac{\sum x_i^2 - \frac{(\sum x_i)^2}{N}}{N}$$

and were used to estimated the means, variance and sample variance, respectively. Comparisons of two proportions were performed by $$U = \frac{p_1 - p_2}{\sqrt{\frac{p_1 q_1}{n} + \frac{p_2 q_2}{m}}}.$$

The Fisher exact test was carried by $$P = \frac{\frac{R_1! R_2! C_1! C_2!}{n!}}{f_{11}! f_{12}! f_{21}! f_{22}!}$$

where $f_{ij}$ denotes the frequency observed in row i and column j, and $R_i$ and $C_j$ are row and column totals, respectively.

The Person Having Ordinary Skill In The Art will appreciate that many of the Steps set forth are known in the Art, so extraneous and redundant details have been omitted for clarity and conciseness. It will also be understood that undisclosed modifications are possible, and those modifications should not be construed as falling outside the scope of the invention.

I claim:

1. A method of detecting certain exons and introns in genome data comprising the steps of:
   a) providing a computer for data identification and comparison purposes, the computer having access to predetermined genome data including nucleotide sequence data, predetermined 5' and 3' splicing junction data, and exon and intron data;
   b) obtaining genome data from biochemical analysis of a test sample or from a database;
   c) computer mediated identification of 5' and 3' splicing junctions in the test sample based on similarities with the predetermined 5' and 3' splicing junctions, wherein the 5' and 3' splicing junctions in the test sample have less than 100% homology with the predetermined 5' and 3' splicing junctions; and
   d) detecting introns and exons of the 5' and 3' splicing junctions in the test sample based on similarities with the introns and exons of the predetermined 5' and 3' splicing junctions.

2. The method of claim 1 wherein the step of identifying 5' and 3' splicing junctions in the test sample comprises the step of identifying 5' and 3' splicing junctions in DNA of the test sample by biochemical analysis.

3. The method of claim 1 wherein the step of identifying 5' and 3' splicing junctions in the test sample comprises the step of identifying 5' and 3' splicing junctions in mRNA of the test sample by biochemical analysis.

4. The method of claim 1 wherein the step of identifying 5' and 3' splicing junctions comprises the step of selecting oligomers which reflect the similarities with 6-15 base pair oligomers of predetermined 5' and 3' splicing junctions.

5. The method of claim 1 wherein the step of identifying 5' and 3' splicing junctions in the test sample comprises the step of employing comparative genomic techniques.

6. The method of claim 5 wherein the step of identifying 5' and 3' splicing junctions in the test sample employing comparative genomic techniques comprises the step of identifying 5' and 3' splicing junctions in the test sample which have at least 99% homology with predetermined 5' and 3' splicing junctions.

7. The method of claim 5 wherein the step of identifying 5' and 3' splicing junctions in the test sample employing comparative genomic techniques comprises the step of identifying 5' and 3' splicing junctions in the test sample which have at least 90% homology with predetermined 5' and 3' splicing junctions.

8. The method of claim 5 wherein the step of identifying 5' and 3' splicing junctions in the test sample employing comparative genomic techniques comprises the step of identifying 5' and 3' splicing junctions in the test sample which have at least 75% homology with predetermined 5' and 3' splicing junctions.

9. The method of claim 5 wherein the step of identifying 5' and 3' splicing junctions in the test sample employing comparative genomic techniques comprises the step of identifying 5' and 3' splicing junctions in the test sample which have at least 50% homology with predetermined 5' and 3' splicing junctions.

10. The method of claim 1 wherein said step of identifying 5' and 3' splicing junctions in the test sample comprises the step of employing electrophoretic techniques.

11. The method of claim 1 further comprising the step of correlating test sample exons and introns with exons and introns associated with diseases.

12. A method of detecting certain exons and introns in genome data comprising the steps of:
 a) providing a computer for data identification and comparison purposes, the computer having access to predetermined genome data including nucleotide sequence data, predetermined 5' and 3' splicing junction data, and exon and intron data;
 b) obtaining genome data from biochemical analysis of a test sample or from a database, selected from the group consisting of DNA and mRNA;
 c) computer mediated identification of 5' and 3' splicing junctions in the test sample by comparative genomic techniques based on similarities with the predetermined 5' and 3' splicing junctions, wherein the 5' and 3' splicing junctions in the test sample have less than 100% homology with the predetermined 5' and 3' splicing junctions; and
 d) detecting introns and exons of the 5' and 3' splicing junctions in the test sample based on similarities with the introns and exons of the predetermined 5' and 3' splicing junctions.

13. The method of claim 12 further comprising the step of correlating test sample exons and introns with exons and introns associated with diseases.

14. The method of claim 13 further comprising the step of predicting increased susceptibility to the diseases based on the correlation.

15. The method of claim 13 further comprising the step of diagnosing the diseases based on the correlation.

* * * * *